United States Patent
Isayev et al.

(10) Patent No.: US 12,373,668 B2
(45) Date of Patent: Jul. 29, 2025

(54) METHODS, SYSTEMS AND NON-TRANSITORY COMPUTER READABLE MEDIA FOR AUTOMATED DESIGN OF MOLECULES WITH DESIRED PROPERTIES USING ARTIFICIAL INTELLIGENCE

(71) Applicant: The University of North Carolina at Chapel Hill, Chapel Hill, NC (US)

(72) Inventors: Olexandr Isayev, Chapel Hill, NC (US); Mariya Popova, Almaty (KZ); Alexander Tropsha, Chapel Hill, NC (US)

(73) Assignee: THE UNIVERSITY OF NORTH CAROLINA AT CHAPEL HILL, Chapel Hill, NC (US)

( * ) Notice: Subject to any disclaimer, the term of this patent is extended or adjusted under 35 U.S.C. 154(b) by 1124 days.

(21) Appl. No.: 16/632,328

(22) PCT Filed: Jul. 20, 2018

(86) PCT No.: PCT/US2018/043114
§ 371 (c)(1),
(2) Date: Jan. 17, 2020

(87) PCT Pub. No.: WO2019/018780
PCT Pub. Date: Jan. 24, 2019

(65) Prior Publication Data
US 2020/0168302 A1 May 28, 2020

Related U.S. Application Data

(60) Provisional application No. 62/535,069, filed on Jul. 20, 2017.

(51) Int. Cl.
*G06N 20/00* (2019.01)
*G06N 3/044* (2023.01)
(Continued)

(52) U.S. Cl.
CPC ............. *G06N 3/045* (2023.01); *G06N 3/044* (2023.01); *G06N 3/088* (2013.01); *G06N 20/00* (2019.01)

(58) Field of Classification Search
CPC ........ G16C 20/50; G16C 20/30; G16C 20/62; G16C 20/70; G06N 3/044; G06N 3/045;
(Continued)

(56) References Cited

U.S. PATENT DOCUMENTS

| | | | |
|---|---|---|---|
| 6,587,845 | B1 | 7/2003 | Braunheim |
| 2006/0161407 | A1 | 7/2006 | Lanza et al. |

(Continued)

OTHER PUBLICATIONS

Guimaraes GL, Sanchez-Lengeling B, Outeiral C, Farias PL, Aspuru-Guzik A. Objective-reinforced generative adversarial networks (organ) for sequence generation models. arXiv preprint arXiv:1705.10843. May 30, 2017. (Year: 2017).*

(Continued)

*Primary Examiner* — Michael J Huntley
*Assistant Examiner* — Sehwan Kim
(74) *Attorney, Agent, or Firm* — Jenkins, Taylor & Hunt, P.A.

(57) ABSTRACT

The subject matter described herein includes computational methods, systems and non-transitory computer readable media for de-novo drug discovery, which is based on deep learning and reinforcement learning techniques. The subject matter described herein allows generating chemical compounds with desired properties. Two deep neural networks-generative and predictive, represent the general workflow. The process of training consists of two stages. During the first stage, both models are trained separately with supervised learning algorithms, and during the second stage, models are trained jointly with reinforcement learning approach. In this study, we conduct a computational experiment, which demonstrates the efficiency of proposed strat- (Continued)

egy to maximize, minimize or impose a desired range to a property. We also thoroughly evaluate our models with quantitative approaches and provide visualization and interpretation of internal representation vectors for both predictive and generative models.

16 Claims, 15 Drawing Sheets

(51) Int. Cl.
  *G06N 3/045* (2023.01)
  *G06N 3/088* (2023.01)
(58) Field of Classification Search
  CPC ........ G06N 3/088; G06N 20/00; G06N 3/048; G06N 3/006; G06N 3/047; G06N 3/08
  See application file for complete search history.

(56) References Cited

U.S. PATENT DOCUMENTS

| | | | | |
|---|---|---|---|---|
| 2010/0010946 | A1* | 1/2010 | De Winter | G16B 15/30 703/1 |
| 2012/0265514 | A1 | 10/2012 | Hopkins et al. | |
| 2013/0252280 | A1 | 9/2013 | Weaver et al. | |

OTHER PUBLICATIONS

Segler MH, Kogej T, Tyrchan C, Waller MP. Generating Focussed Molecule Libraries for Drug Discovery with Recurrent Neural Networks. arXiv preprint arXiv:1701.01329. Jan. 5, 2017. (Year: 2017).*
Joulin, Armand, and Tomas Mikolov. "Inferring algorithmic patterns with stack-augmented recurrent nets." Advances in neural information processing systems 28 (2015). (Year: 2015).*
Yu, Lantao, et al. "Seqgan: Sequence generative adversarial nets with policy gradient." Proceedings of the AAAI conference on artificial intelligence. vol. 31. No. 1. 2017. (Year: 2017).*
Jaques, Natasha, et al. "Tuning recurrent neural networks with reinforcement learning." (2017). (Year: 2017).*
Olivecrona, Marcus, et al. "Molecular de-novo design through deep reinforcement learning." Journal of cheminformatics 9.1 (2017): 1-14. (Year: 2017).*
Jaques, Natasha, et al. "Sequence tutor: Conservative fine-tuning of sequence generation models with kl-control." International Conference on Machine Learning. PMLR, 2017. (Year: 2017).*
Yuan, William, et al. "Chemical space mimicry for drug discovery." Journal of chemical information and modeling 57.4 (2017): 875-882. (Year: 2017).*
Duvenaud, David K., et al. "Convolutional networks on graphs for learning molecular fingerprints." Advances in neural information processing systems 28 (2015). (Year: 2015).*
Lei, Tao, et al. "Deriving neural architectures from sequence and graph kernels." International Conference on Machine Learning. PMLR, 2017. (Year: 2017).*
Bjerrum, Esben Jannik, and Richard Threlfall. "Molecular generation with recurrent neural networks (RNNs)." arXiv preprint arXiv:1705. 04612 (2017). (Year: 2017).*
Gómez-Bombarelli, Rafael, et al. "Automatic chemical design using a data-driven continuous representation of molecules." arXiv:1610. 02415, 2016 (Year: 2016).*
"Scientific Databases," SRC, Inc., https://www.srcinc.com/what-we-do/environmental/scientific-databases.html, pp. 1-4 (2020).
Mullard, "The Drug-Maker's Guide to the Galaxy," Nature, vol. 549, pp. 445-447 (Sep. 28, 2017).
"Introduction to MarvinSketch," https://docs.chemaxon.com/display/docs/Introduction_to_MarvinSketch.html, pp. 1-7 (Accessed Jul. 20, 2017).

"Murcko Scaffolds," Datagrok, https://datagrok.ai/help/domains/chem/functions/murcko-scaffolds, pp. 1-1 (Accessed Jul. 20, 2017).
Stumpfe et al., "Similarity Searching," Wiley Interdiscip. Rev. Compt. Mol. Sci., vol. 1, pp. 260-282 (2011).
"Zinc263823677," Zinc 15, http://zinc15.docking.org/substances/ZINC000263823677/, pp. 1-10 (2021).
"ZinC271402431," Zinc 15, http://zinc15.docking.org/substances/ZINC271402431/, pp. 1-10 (2021).
"Kinase Knowledgebase (KKB)," Eidogen Seranty, pp. 1-2 (2021).
"Reinforcement Learning," Wikipedia, pp. 1-16 (Sep. 16, 2021).
Popova et al., "Deep Reinforcement Learning for de-novo Drug Design," Science Advances, pp. 1-28 (2018).
"Chemotext," Chemotext, http://chemotext.mml.unc.edu/, pp. 1-2 (Nov. 8, 2017).
Marblestone et al., "Automatically inferring scientific semantics," MIT, The Wayback Machine https://web.archive.org/web/20160709144625/http://web.mit.edu/amarbles/www/neuro_word2vec.html, pp. 1-2 (Jul. 2016).
McCormick, "Word2Vec Tutorial—The Skip-Gram Model," Chris McCormick, http://mccormickml.com/2016/04/19/word2vec-tutorial-the-skip-gram-model/, pp. 1-21 (Apr. 19, 2016).
De Asis et al., "Multi-Step Reinforcement Learning: A Unifying Algorithm," The Thirty-Second AAAI Conference on Artificial Intelligence, pp. 2902-2909 (2018).
Gomez-Bombarelli et al., "Automatic Chemical Design Using a Data-Driven Continuous Representation of Molecules," ACS Cent. Sci., vol. 4, pp. 268-276 (2018).
Segler et al., "Generating Focused Molecule Libraries for Drug Discovery with Recurrent Neural Networks," ACS Cent. Sci., vol. 4, pp. 120-131 (2018).
Ragoza et al., "Protein-Ligand Scoring with Convolutional Neural Networks," J Chem Inf Model, vol. 57, No. 4, pp. 1-50 (Apr. 24, 2017).
Altae-Tran et al., "Low Data Drug Discovery with One-Shot Learning," ACS Cent. Sci., vol. 3, pp. 283-293 (Apr. 3, 2017).
Segler et al., "Modelling Chemical Reasoning to Predict and Invent Reactions," Chem. Eur. J., vol. 23, pp. 6118-6128 (2017).
Smith et al., "ANI-1: an extensible neural network potential with DFT accuracy at force field computational cost," Chem. Sci., vol. 8, pp. 3192-3203 (2017).
Yu et al., "SeqGAN: Sequence Generative Adversarial Nets with Policy Gradient," Proceedings of the Thirty-First AAAI Conference on Artificial Intelligence, pp. 2852-2858 (2017).
Nguyen et al., "Pharos: Collating protein information to shed light on the druggable genome," Nucleic Acids Research, vol. 45, pp. D995-D1002 (2017).
Santos et al., "A comprehensive map of molecular drug targets," Nat Rev Drug Discov., vol. 16, No. 1, pp. 1-32 (Jan. 2017).
Chockley et al., "The End of Radiology? Three Threats to the Future Practice of Radiology," J Am Coll Radiol, vol. 13, pp. 1415-1420 (2016).
Deleu et al., "Learning Operations on a Stack with Neural Turing Machines," arXiv:1612.00827v1, pp. 1-6 (Dec. 2, 2016).
Jha et al., "Adapting to Artificial Intelligence Radiologists and Pathologists as Information Specialists," Jama, pp. 1-2 (Nov. 29, 2016).
Krakovsky, "Reinforcement Renaissance," Communications of the ACM, vol. 59, No. 8, pp. 12-14 (Aug. 2016).
Morgenstern, "Artificial Intelligence," The Economist, https://www.economist.com/special-report/2016/06/23/the-return-of-the-machinery-question, pp. 1-5 (Jun. 23, 2016).
Longo et al., "Data Sharing," The New England Journal of Medicine, vol. 374, No. 3, pp. 276-277 (Jan. 21, 2016).
Schneider et al., "De Novo Design at the Edge of Chaos," Journal of Medicinal Chemistry, vol. 59, pp. 4077-4086 (2016).
Ursu et al., "DrugCentral: online drug compendium," Nucleic Acids Research, vol. 25, pp. D932-D939 (2017).
Wang et al., "PubChem BioAssay: 2017 Update," Nucleic Acids Research, vol. 45, pp. D955-D963 (2017).
Low et al., "Cheminformatics-aided pharmacovigilance: application to Stevens-Johnson Syndrome," J Am Med Infom Assoc, vol. 23, pp. 1-11 (2016).

(56) References Cited

OTHER PUBLICATIONS

Rastegar-Mojarad et al., "Using Social Media Data to Identify Potential Candidates for Drug Repurposing: A Feasibility Study," JMIR Res Protoc, vol. 5, No. 2, pp. 1-12 (2016).
Silver et al., "Mastering the game of Go with deep neural networks and tree search," Nature, vol. 529, pp. 1-20 (Jan. 28, 2016).
Joulin et al., Inferring Algorithmic Patterns with Stack-Augmented Recurrent Nets, arXiv, pp. 1-10 (2015).
Oprea et al., "Computational and Practical Aspects of Drug Repositioning," Assay and Drug Development Technologies, vol. 13, No. 6, pp. 299-306 (Jul./Aug. 2015).
Reker et al., "Active-learning strategies in computer-assisted drug discovery," Drug Discovery Today, vol. 20, No. 4, pp. 458-465 (Apr. 2015).
Grefenstette et al., "Learning to Transduce with Unbounded Memory" arXiv, pp. 1-9 (2015).
Goodfellow et al., "Generative Adversarial Nets," Adv. Neural Inf. Process. Syst., No. 27, pp. 1-9 (2014).
Spangler et al., "Automated Hypothesis Generation Based on Mining Scientific Literature," KDD '14, pp. 1877-1886 (Aug. 24-27, 2014).
Tetko et al., "How Accurately Can We Predict the Melting Points of Drug-like Compounds?," Journal of Chemical Information and Modeling, pp. 1-11 (Dec. 2014).
Chung et al., "Empirical Evaluation of Gated Recurrent Neural Networks on Sequence Modeling," arXiv:1412.3555v1, pp. 1-9 (Dec. 11, 2014).
Bento et al., "The ChEMBL bioactivity database: an update," Nucleic Acids Research, vol. 42, pp. D1083-D1090 (Nov. 7, 2013).
Yom-Tov et al., "Postmarket Drug Surveillance Without Trial Costs: Discovery of Adverse Drug Reactions Through Large-Scale Analysis of Web Search Queries," J Med Internet Res, vol. 15, No. 6, pp. 1-12 (2013).
Mikolov et al., "Distributed Representations of Words and Phrases and their Compositionality," Nips, pp. 1-9 (2013).
Mikolov et al., "Efficient Estimation of Word Representations in Vector Space," arXiv:1301.3781v3, pp. 1-12 (Sep. 7, 2013).
Polishchuk et al., "Estimation of the size of drug-like chemical space based on GDB-17," J Comput Aided Mol Des, vol. 27, pp. 675-679 (2013).
Scannell, "Diagnosing the decline in pharmaceutical R&D efficiency," Nature Reviews, Drug Discovery, vol. 11, pp. 191-200 (Mar. 2012).
Ruddigkeit et al., "Enumeration of 166 Billion Organic Small Molecules in the Chemical Universe Database GDB-17," Journal of Chemical Information and Modeling, vol. 52, pp. 2864-2875 (2012).
Sutskever et al., "Generating Text with Recurrent Neural Networks," Proceedings of the 28th International Conference on Machine Learning, pp. 1-8 (2011).
Baker et al., "Mining connections between chemicals, proteins, and diseases extracted from Medline annotations," Journal of Biomedical Informatics, vol. 43, pp. 510-519 (2010).
Fourches et al., "Trust, but verify: On the importance of chemical structure curation in cheminformatics and QSAR modeling research," J Chem Inf Model, vol. 50, No. 7, pp. 1-37 (Jul. 26, 2010).
Mauser et al., "Recent developments in de novo design and scaffold hopping," Current Opinion in Drug Discovery & Development, vol. 11, No. 3, pp. 365-374 (2008).
Van der Maaten et al., "Visualizing Data using t-SNE," Journal of Machine Learning Research, vol. 9, pp. 2579-2605 (2008).
Berstel, "Transductions and Context-Free Languages," Teubner-Verlag, pp. 1-139 (Feb. 19, 2007).
Macarron, "Critical review of the role of HTS in drug discovery," Drug Discovery Today, vol. 11, Nos. 7/8, pp. 277-279 (Apr. 2006).
Schnecke et al., "Computational chemistry-driven decision making in lead generation," DDT, vol. 11, No. 1/2 , pp. 44-50 (Jan. 2006).
Irwin et al., "Zinc-A Free Database of Commercially Available Compounds for Virtual Screening," J Chem Inf Model., vol. 45, No. 1, pp. 1-11 (2005).
Schneider et al., "Computer-Based De Novo Design of Drug-Like Molecules," Nature Reviews, Drug Discovery, vol. 4, pp. 649-663 (Aug. 2005).
Kralovics et al., "A Gain-of-Function Mutation of JAK2 in Myeloproliferative Disorders," The New England Journal of Medicine, vol. 352, pp. 1779-1790 (2005).
Lipinski et al., "Navigating chemical space for biology and medicine," Nature, vol. 432, pp. 1-8 (Dec. 16, 2004).
Brown et al., "A Graph-Based Genetic Algorithm and Its Application to the Multiobjective Evolution of Median Molecules," J. Chem. Inf. Comp. Sci., vol. 44, pp. 1079-1087 (2004).
Van den Herik et al., "Games solved: Now and in the future," Artificial Intelligence, vol. 134, pp. 277-311 (2002).
Hochreiter et al., "Long Short-Term Memory," Neural Computation, vol. 9, No. 8, pp. 1735-1780 (1997).
Sakatsume et al., "The Jak Kinases Differentially Associate with the α and β (Accessory Factor) Chains of the Interferon γ Receptor to Form a Functional Receptor Unit Capable of Activating STAT Transcription Factors*," The Journal of Biological Chemistry, vol. 270, No. 29, pp. 17528-17534 (Jul. 21, 1995).
Williams, "Simple Statistical Gradient-Following Algorithms for Connectionist Reinforcement Learning," Machine Learning, vol. 8, pp. 229-256 (1992).
Swanson et al., "Medical literature as a potential source of new knowledge*," Bull Med Libr Assoc, vol. 78, No. 1, pp. 29-37 (Jan. 1990).
Weininger, "Smiles, a Chemical Language and Information System. 1. Introduction to Methodology and Encoding Rules," J. Chem. Inf. Comput. Sci., vol. 28, No. 1, pp. 31-36 (1988).
Notification of Transmittal of the International Search Report and the Written Opinion of the International Searching Authority, or the Declaration for International Application No. PCT/US2018/043114 (Oct. 15, 2018).
Bjerrum, "Smiles Enumeration as Data Augmentation for Neural Network Modeling of Molecules," Cornell University Library, Computer Science, Machine Learning, arXiv:1703.07076, pp. 1-7 (May 17, 2017).
Olivecronia et al., "Molecular De-Novo Design through Deep Reinforcement Learning," Cornell University Library, Computer Science, Artificial Intelligent, arXiv:1704.07555, pp. 1-16 (Apr. 25, 2017).

* cited by examiner

METHODS, SYSTEMS AND NON-TRANSITORY COMPUTER READABLE MEDIA FOR AUTOMATED DESIGN OF MOLECULES WITH DESIRED PROPERTIES USING ARTIFICIAL INTELLIGENCE

PRIORITY CLAIM

This application claims the priority benefit of U.S. Provisional Patent Application Ser. No. 62/535,069 filed Jul. 20, 2017, the disclosure of which is incorporated herein by reference in its entirety.

GOVERNMENT INTEREST

This invention was made with government support under grant number N0014-16-1-2311 awarded by the Office of Naval Research and grant number ACI-1053575 awarded by the National Science Foundation. The government has certain rights in the invention.

TECHNICAL FIELD

The subject matter described herein relates to molecule design. More particularly, the subject matter described herein relates to methods, systems, and non-transitory computer readable media for automated design of molecules with desired properties using artificial intelligence.

BACKGROUND

The analysis of recent trends in drug development and approval presents rather bleak picture.[1] The approval of new drugs has been flat over the last two decades. Less than one out of every 10,000 drug candidates becomes an approved marketed drug. Only three out of every 20 approved drugs bring in enough revenue to cover developmental costs. Moreover, it takes approximately 10-15 years and an average cost of $1-3 billion to develop each new drug. Many promising drug candidates fail in phase II and phase III— later stages of the clinical development process. These high attrition rates at a time when projects have already incurred high costs make for very expensive failures. This so-called innovation gap can be attributed to several challenges ranging from drug safety concerns, lack of efficacy to great complexity of diseases and tightened regulations. Thus, pharmaceutical industry is currently challenged to increase the efficiency of drug development.

Increasingly scientific advancements are more subject to error and harder to reproduce. Human activities are identified as a principal bottleneck in technological innovations, which leads to inefficiencies, potential errors, and incomplete explorations of the hypothesis and data analysis space. Artificial intelligence (AI) systems can radically transform the practice of scientific discovery. The combination of big data and artificial intelligence, referred to by some as the fourth industrial revolution.[2] Today as machine learning also enables our computers to teach themselves drive cars or automatically understand speech. AI is revolutionizing radiology, pathology along with other medical specialties.[3,4] Application of Deep Learning (DL) see significant improvement in docking scoring[5], learning from small data[6], reaction mechanism[7] and energy prediction.[8]

The drug discovery pipeline is notoriously sequential. Hits from a high throughput screen (HTS) are slowly progressed toward promising lead compounds. Next, the ADMET and selectivity profile is optimized with a challenge to maintain high potency and efficacy. High failure rates in late-stage clinical trials could be potentially avoided if the relevant information were available earlier or if the available data could provide clues as to whether a drug will actually perform as expected in clinical practice. The crucial step is the formulation of a well-motivated hypothesis for compound generation (de novo design) or compound picking from a library based on the available SAR data. Commonly, an interdisciplinary team of scientists generates the new hypothesis by relying on their expertise and medicinal chemistry intuition. Therefore, any design hypothesis is easily biased towards preferred chemistry[9] or model interpretation.[10]

The idea of automated drug design is not new.[11,12] It has contributed to drug discovery projects since the 2000s by suggesting novel molecular structures with desired properties from scratch and has become an active field of research. In an attempt to design new compounds, both a medicinal chemist and algorithm is confronted with a virtually infinite chemical space. Today, the range of potential drug-like molecules is estimated to be between $10^{30}$ and $10^{60}$.[13,14] Unfortunately, such a large space prohibits exhaustive searching, despite great advances in high-throughput screening (HTS) technology.[15] Instead of the systematic construction and evaluation of each individual compound, navigation in the de novo design process relies on the principle of local optimization, which does not necessarily lead to the optimal solution: the design process converges on a local or 'practical' optimum by stochastic sampling or restricts the search to a defined section of chemical space which can be screened exhaustively.[11,16-18] However, recently, a method for exploring chemical space based on continuous encodings of molecules was proposed.[19] It allows directed gradient-based search through chemical space. Another method of generating focused molecule libraries with Recurrent Neural Networks is also proposed.[20]

SUMMARY

Here we propose a novel method based on deep reinforcement learning (RL) for generating chemical compounds with desired physical, chemical or bioactivity properties. Reinforcement learning (RL) is a subset of artificial intelligence, which is used to solve dynamic decision problems. RL involves analyzing possible actions, estimating the statistical relationship between the actions and their possible outcomes and then determining a treatment regime that attempts to find the most desirable outcome based on the analysis The integration of reinforcement learning and neural networks dated back to 1990s [21]. However, with recent achievements of DL, benefiting from big data, new powerful algorithmic approaches are emerging. We are currently witnessing the renaissance of reinforcement learning [22], especially the combination of reinforcement learning and deep neural networks, i.e., deep reinforcement learning (Deep RL). Most recently RL has led to superhuman performance in game Go,[23] considered practically intractable due to the theoretical complexity of over $10^{140}$.[24] Therefore, we see an example of attacking a problem of the difficulty comparable to a chemical space exploration without brute-force computing every possible solution.

The subject matter described herein may be implemented in software in combination with hardware and/or firmware. For example, the subject matter described herein may be implemented in software executed by a processor, which may be a general-purpose processor, a special purpose processor, such as a graphics processing unit (GPU) or a field programmable gate array (FPGA). In one exemplary implementation, the subject matter described herein may be implemented using a computer readable medium having stored thereon computer executable instructions that when executed by the processor of a computer control the computer to perform steps. Exemplary computer readable media suitable for implementing the subject matter described herein include non-transitory devices, such as disk memory devices, chip memory devices, programmable logic devices, and application specific integrated circuits. In addition, a computer readable medium that implements the subject matter described herein may be located on a single device or computing platform or may be distributed across multiple devices or computing platforms.

DETAILED DESCRIPTION

Figure 1:
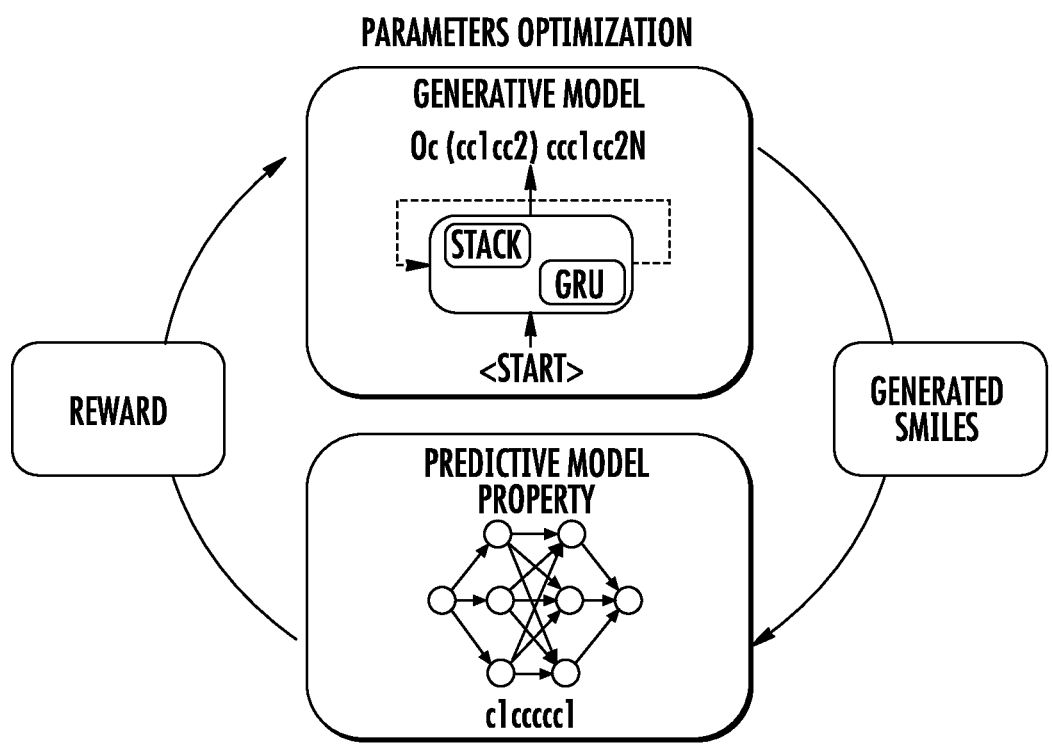
FIG. 1 is a block diagram of a general workflow for a reinforcement learning system for novel molecule generation.

The subject matter described herein includes an RL-based de novo design method for generating chemical compounds with desired physical, chemical or bioactivity properties. The general workflow (FIG. 1) is represented by two deep neural networks (generative G and predictive P). The process of training consists of two stages. During the first stage, both models are trained separately with supervised learning algorithms, and during the second stage, the models are trained jointly with a reinforcement learning approach optimizing target properties. In this system, the generative model plays the role of agent. The predictive model plays the role of critic, which estimates the agent's behavior by assigning a numerical reward to every generated molecule. The reward is a function of the numerical property predicted by the predictive model. The generative model is trained to maximize the expected reward. The components illustrated in FIG. 1 can be implemented on a computing platform including at least one processor.

Reinforcement learning formulation. Both generative G and predictive model P are combined into one RL system. The set of actions A is defined as an alphabet of SMILES notation. The set of states S is defined as all possible strings in the alphabet with lengths from 0 to some T. The state $s_0$ with length 0 is unique and considered to be an initial state. The state $s_T$ of length T is called the terminal state and it causes an episode to end. The subset of terminal states $S^* = \{s_T \in S\}$ of S which contains all the states $S_T$ with length T is called the terminal states set. The reward $r(s_T)$ is calculated at the end of an episode when terminal state is reached. Intermediate rewards $r(s_T)$, $t<T$ are equal to 0. In these terms, the generator network G can be treated as a policy approximation model. At each time step t, $0<t<T$, G takes previous state $s_{t-1}$ as an input and estimates probability distribution $p(a_t|s_{t-1})$ of the next action. Afterwards, the next action at is sampled from this estimated probability. Reward $r(s_T)$ is a function of the predicted property of $s_T$ by the predictive model P.

$$r(s_T) = f(P(s_T)),$$

where $f$ is chosen expertly depending on the task. Some examples of the functions $f$ are provided further in the computational experiment section. Given these notations and assumptions, the problem of generating chemical compounds with desired properties can be formulated as a task of finding a vector of parameters $\Theta$ of policy network G which maximizes the expected reward:

$$J(\Theta) = \mathbb{E}[r(s_T) \mid s_0, \Theta] = \sum_{s_T \in S^*} p_\Theta(s_T) r(s_T) \to \max. \quad (1)$$

This sum iterates over the set S* of terminal states. In our case, this set is exponential and the sum cannot be exactly computed. According to the law of large numbers, we can approximate this sum as a mathematical expectation by sampling terminal sequences from the model distribution:

$$J(\Theta) = \mathbb{E}[r(s_T)|s_0, \Theta] = \mathbb{E}_{a_1 \sim p_\Theta(a_1|s_0)} \mathbb{E}_{a_2 \sim p_\Theta(a_2|s_1)} \cdots$$
$$\mathbb{E}_{a_T \sim p_\Theta(a_T|s_{T-1})} r(s_T).$$

The procedure for $J(\Theta)$ estimation is as follows: sequentially sample $a_t$ from the model G for t from 0 to T. The unbiased estimation for $J(\Theta)$ is the sum of all rewards in every time step, which in our case equals the reward for the terminal state, as we assume that intermediate rewards are equal to 0. As this quantity needs to be maximized, we need to compute its gradient. This can be done, for example with a REINFORCE algorithm[25] which uses approximation of mathematical expectation as a sum, which we provided above, and the following trick:

$$\partial_\Theta f(\Theta) = f(\Theta) \frac{\partial_\Theta f(\Theta)}{\partial \Theta} = f(\Theta) \partial_\Theta \log f(\Theta).$$

Therefore, the gradient of $J(\Theta)$ can be written as:

$$\partial_\Theta J(\Theta) = \sum_{s_T \in S^*} [\partial_\Theta p_\Theta(s_T)] r(s_T) = \sum_{s_T \in S^*} p_\Theta(s_T)[\partial_\Theta \log p_\Theta(s_T)] r(s_T) =$$

$$\sum_{s_T \in S^*} p_\Theta(s_T) \left[ \sum_{t=1}^{T} \partial_\Theta \log p_\Theta(a_t \mid s_{t-1}) \right] r(s_T) = \mathbb{E}_{a_1 \sim p_\Theta(a_1 \mid s_0)}$$

$$\mathbb{E}_{a_2 \sim p_\Theta(a_2 \mid s_1)} \cdots \mathbb{E}_{a_T \sim p_\Theta(a_T \mid s_{T-1})} \left[ \sum_{t=1}^{T} \partial_\Theta \log p_\Theta(a_t \mid s_{t-1}) \right] r(s_T),$$

which gives an algorithm for $\partial_\Theta J(\Theta)$ estimation.

Neural networks architectures. The first model G is a generative recurrent neural network [26-28], which outputs molecules in the simplified molecular-input line-entry system (SMILES) notation[29]. We use a special type of recurrent neural network, referred to as a stack-augmented recurrent neural network (Stack-RNN) [30].

Regular recurrent neural networks like LSTM[31] and GRU[32] fail to solve the sequence prediction problems due to their inability to count. One of the challenging examples of sequences which cannot be properly modeled by a regular recurrent network is words from the Dyck language, a language of balanced strings of brackets[33,34]. Another weakness of regular recurrent neural networks is their inability to capture long term dependencies, which leads to difficulties in generalizing to longer sequences [35]. All of these properties are required to learn the language of SMILES notation. In a valid SMILES molecule, in addition to having the correct valence for all atoms, one must count ring openings and closures, as well as bracket sequences with several bracket types. Therefore, Stack RNNs are a proper choice for modeling such sequence dependencies.

The Stack-RNN defines (See FIG. 2) a new neuron or cell structure on top of a standard GRU cell. It has two additional multiplicative gates, referred to as the memory stack, which allow the Stack-RNN to learn meaningful long-range interdependencies. The stack is a differentiable structure onto and from which continuous vectors are pushed and popped. These traditionally discrete operations are continuous here by letting push and pop operations be real values in the interval (0, 1). Intuitively, we can interpret these values as the degree of certainty with which some controller wishes to push a vector v onto the stack or pop from the top of the stack.

Figure 2:
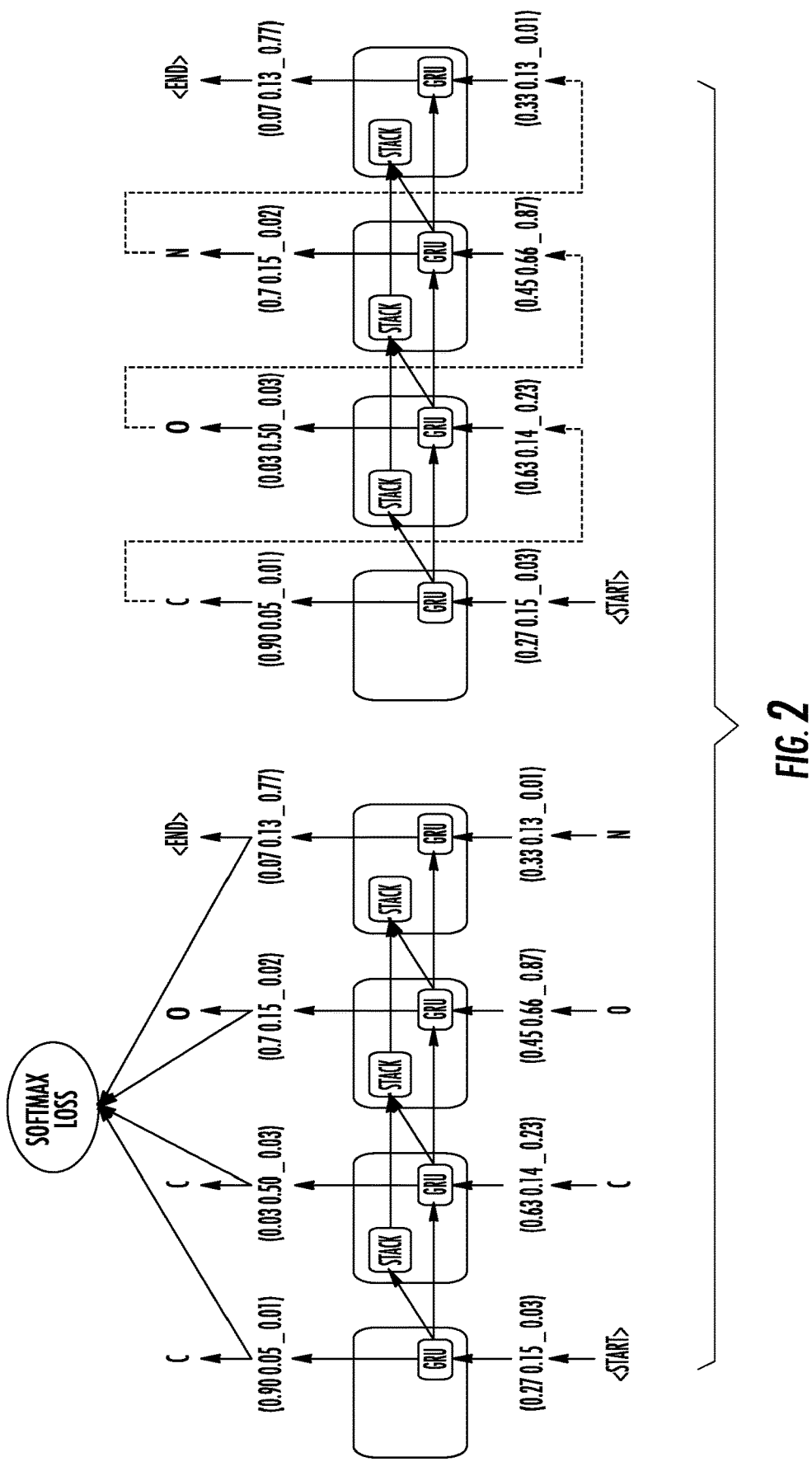
FIG. 2 is a diagram of a generative stack augmented RNN for use in the generative modeler illustrated in FIG. 1; The left hand diagram in FIG. 2 illustrates the training step of the generative stack-augmented RNN; The right hand diagram in FIG. 2 illustrates the generator step of the generative stack-augmented RNN.

FIG. 2 illustrates, on the left hand side, the scheme of a generative stack-augmented RNN time step. This model has two modes—training and generating. During training, the input token is a character of the currently processed SMILES string from the training set. The model outputs probability vector $p_\Theta(a_t | s_{t-1})$ of the next character given the prefix. A vector of parameters $\Theta$ is optimized by a cross-entropy loss function minimization. During generating, the input token is a previously generated character. A next character $a_t$ is sampled randomly from the distribution $p_\Theta(a_t | s_{t-1})$. The right hand side of FIG. 2 illustrates the scheme of the predictive model. This model takes a SMILES string as an input and provides one real number, which is an estimated property value, as an output. Parameters of the model are trained by $l_2$ squared loss function minimization.

The second model P is a predictive model (see FIG. 1) for estimating physical, chemical or bioactivity properties of molecules. This property prediction model is a deep neural network, which consists of an embedding layer [36], LSTM layer and two dense layers. This network is designed to calculate a user-specified property (activity) of the molecule taking the SMILES string as an input data vector. The advantage of such approach is that no numerical descriptors are needed, as it learns directly from SMILES notation.

Results

Figure 3:
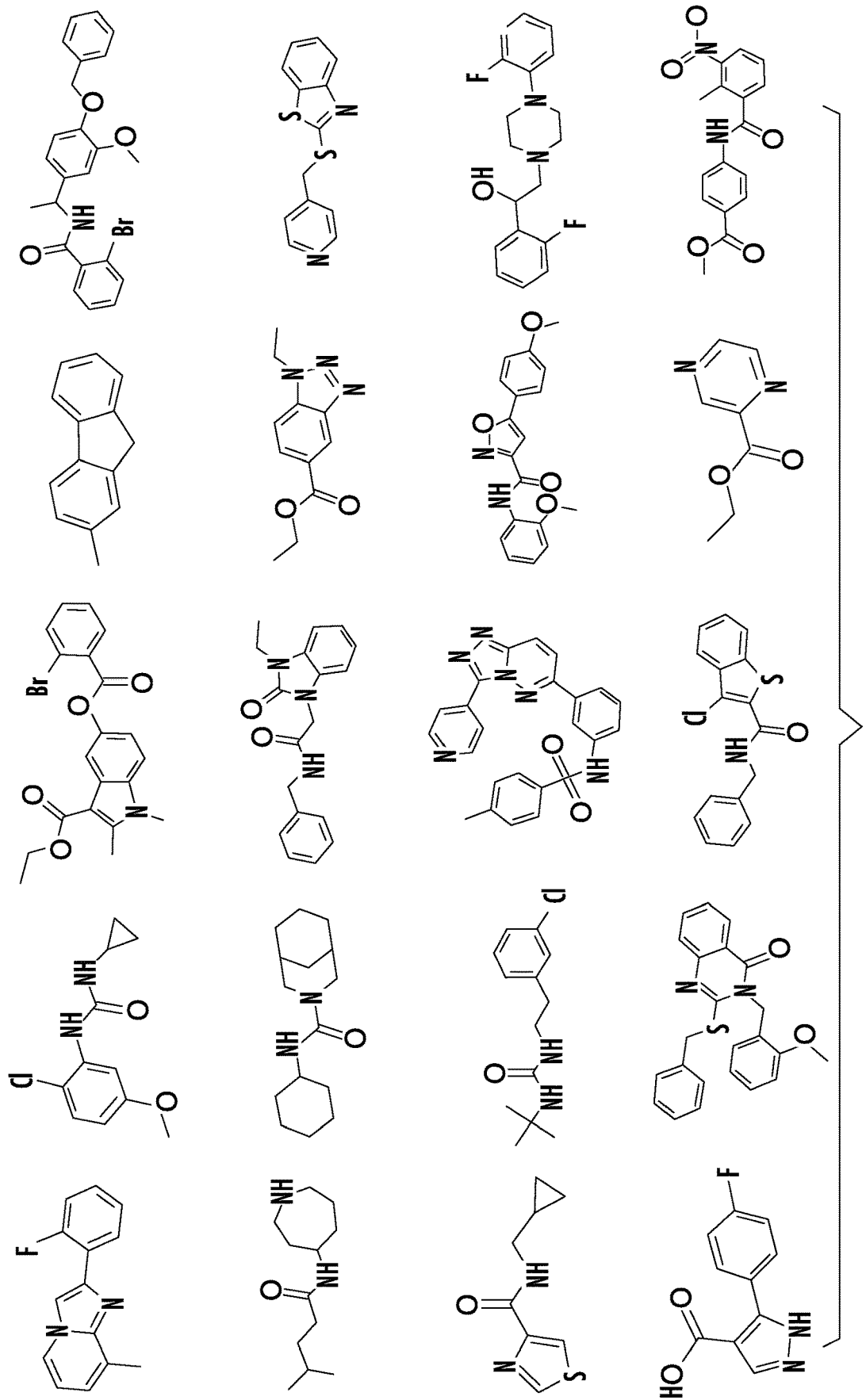
FIG. 3 is a diagram illustrating sample molecules generated by the generative modeler in FIG. 1.
Figure 4A:
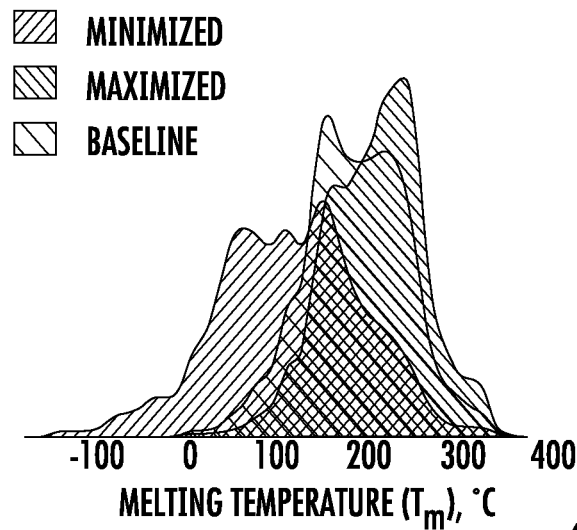
FIG. 4 illustrates graphs of distributions for properties of un-optimized and untrained data.
Figure 4B:
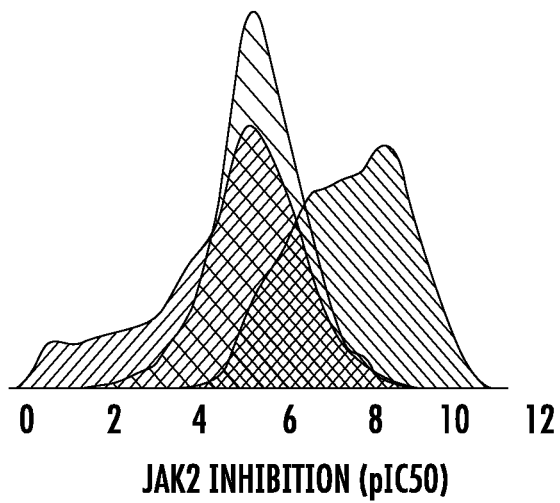
Figure 4C:
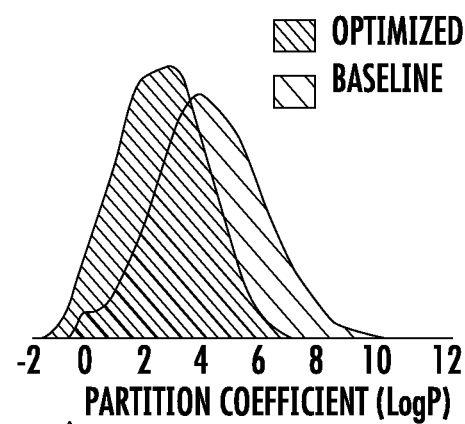
Figure 4D:
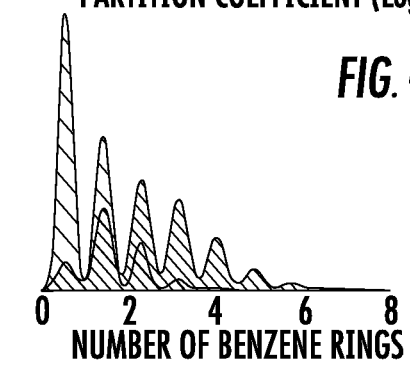
Figure 4E:
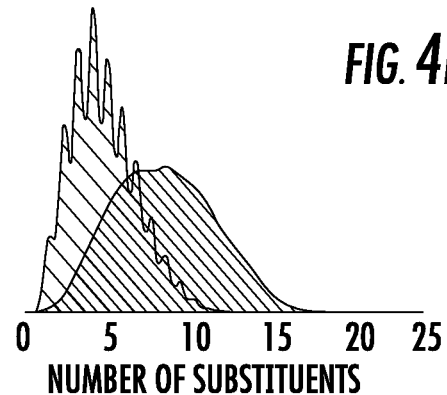

Unbiased molecule generation. To demonstrate the versatility of the baseline (unbiased) Stack RNN, we generated a dataset of over one million virtually synthesized compounds. All structures are available for download from [https://www.dropbox.com/s/ghd668rulye6rxu/1M_dataset.zip?dl=0]. Random examples of the generated compounds are illustrated in FIG. 3.

Over 95% of generated structures were valid chemically sensible molecules. The validity check was performed by the structure checker from ChemAxon[37]. When compared with ChEMBL (See Methods), model produced less than 0.1% of structures from the training dataset. Additional comparison with ZINC15 database[38] of 320M synthetically accessible drug-like molecules show match of about 2% structures.

In order to understand the novelty of the de novo generated molecules, we analyzed the Murcko scaffolds[39] between the training and the virtual molecules. Murcko scaffolds provide a hierarchical molecular organization scheme by dividing small molecules into R-groups, linkers, and frameworks or scaffolds. They contain the ring systems of a molecule by removing side chain atoms. We find that less than 10% scaffolds are present in ChEMBL. Overall, this analysis suggests that the generative Stack RNN model did not simply memorize training SMILEs sequences but is capable of generating extremely diverse but realistic molecules.

RL system. To explore the utility of the RL algorithm in a drug design setting we have set up a multiple case studies that optimize three types of rewards: a) physical property, b) biological activity and c) chemical substructure. For physical properties, we selected melting temperature ($T_m$) and n-octanol/water partition coefficient (log P). Inhibition potency in form of IC50 to Janus kinase 2 or JAK2 was used as biological activity. IC50 is the concentration of drug that is required to inhibit 50% of a specific biological target in vitro. Finally, number of benzene rings and number of substituents (like —OH, —NH$_2$, —CH$_3$—CN, etc.) was used as a structural reward. FIG. 4 shows distributions of predicted properties of interest before and after experiments. In both cases, we sampled 10,000 molecules by the untrained and optimized generative models and calculated their properties with a corresponding predictive model. Values of the substructure features were calculated directly from the 2D structure. Table 1 summarizes analysis of generated molecules and descriptive statistics.

Melting temperature. In this experiment, we set two goals to minimize and maximize the target property. Upon minimization the mean of the distribution was shifted by 44° C. Optimized generator virtually synthesized simple hydrocarbons like butane, and poly-halogenated compounds $CF_2Cl_2$ and $C_6H_4F_2$. $CF_4$ molecule has the lowest $T_m$=−184° C. in the produced dataset. This property minimization strategy is extremely effective, it allowed discovery of molecules in the regions of chemical space far beyond available in the training examples. In the maximization regime mean of the melting temperature is increased by 20° C. to 200° C. The generator synthesized substantially more complex molecules with an abundance of sulfur heterocycles, phosphates as well as conjugated double bonds. The reward functions in both cases are defined as piecewise linear function from melting temperature (see FIG. 11).

log P. To better mimic requirements of drug-likeliness instead of property minimization, we imposed to the range. The reward function in this case was defined as a piecewise linear function of log P with a constant region from 1.0 to 4.0 (see FIG. 11). In other words, we set the goal to uniformly synthesize molecules according to typical Lipinski's constraints. After training, 88% of generated molecules were within the drug-like region between 0 and 5.

Inhibition of JAK2 kinase. In the third experiment, perhaps most relevant to the practical drug discovery application, we directly minimized and maximized pIC50 values for JAK2 kinase. JAK2 is non-receptor tyrosine kinase involved in various processes, such as cell growth, development, differentiation or histone modifications. It mediates essential signaling events in both innate and adaptive immunity. In the cytoplasm it also plays an important role in signal transduction.[40] Mutations in JAK2 have been implicated in multiple conditions like thrombocythemia, myelofibrosis or myeloproliferative disorders.[41]

The reward function in both cases (min and max) was defined as exponential functions of pIC50 (see FIG. 11). The results of optimization are demonstrated in FIG. 11, graph (c). With minimization, the mean of predicted pIC50 distribution was shifted by about one unit. However, the distribution is heavily tailed, and 24% of the molecules are predicted to have practically no activity (pIC50<=4). In the maximization strategy, properties of generated molecules were a more tightly distributed bet. In both cases, models virtually synthesized known and novel compounds based on one scaffold as well as suggested new scaffolds.

The generation of known compounds (i.e., not included in the training set) can be regarded as model validation. Indeed, the system retrospectively discovered 793 commercially available compounds deposited in the ZINC database, which constituted about 5% of the total generated library. Importantly, as many as 15 of them (exemplified by ZINC263823677-http://zinc15.docking.org/substances/ZINC000263823677/and ZINC271402431-http://zinc15.docking.org/substances/ZINC000271402431/) were actually annotated as possible tyrosine kinase inhibitors.

Figure 5A:
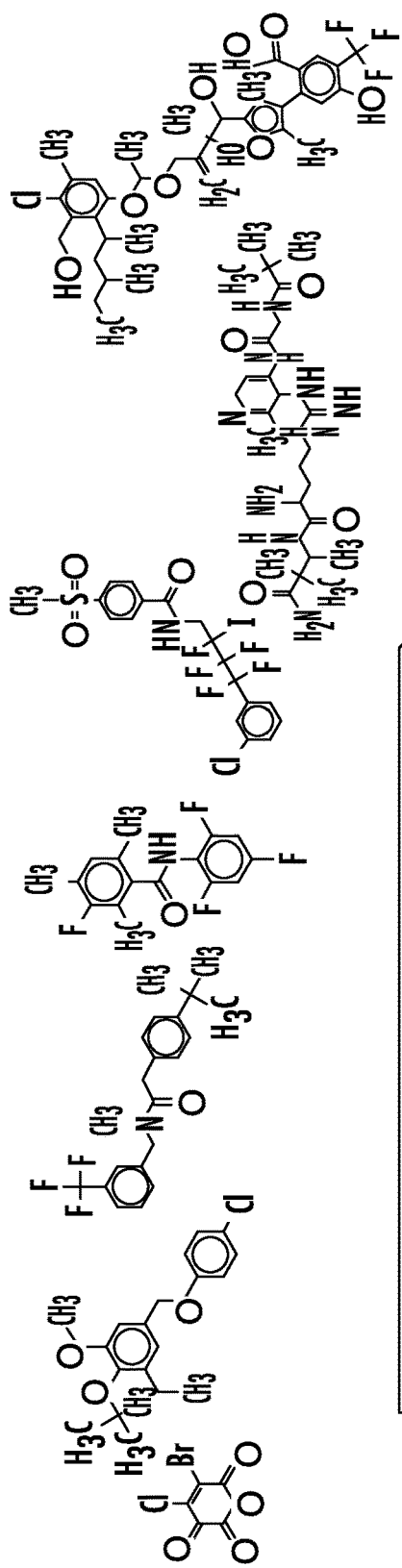
FIG. 5 illustrates the evolution of generated structures as a chemical substructure reward increases.
Figure 5B:
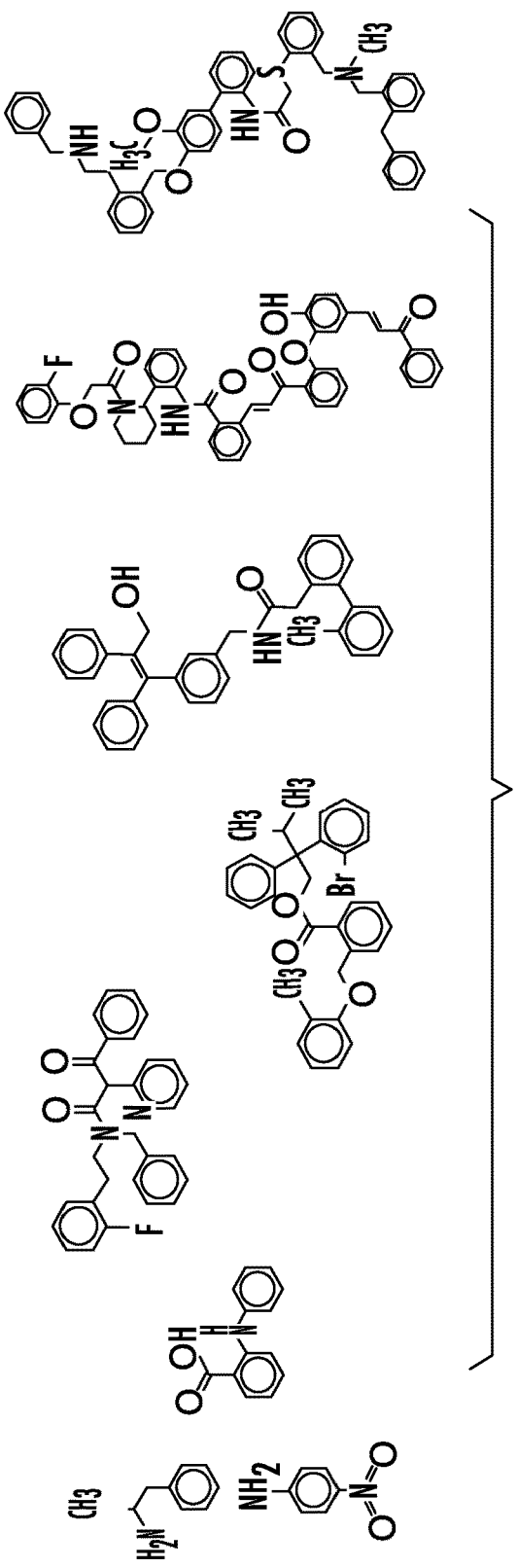

Substructure bias. Finally, we also performed two simple experiments mimicking biasing chemical libraries to a user-defined substructure without predicting any property. We defined the reward function as the exponent of a) number of benzene rings (-Ph) and b) total number of small groups substituents. Among all case studies described, structure bias was the easiest to optimize. FIG. 5 illustrates evolution of generated structures as structural reward increases. We see that the model progresses to generate increasingly complex molecules while maintaining realistic chemistry without very small or large rings.

In realistic drug discovery applications, a substructure bias could be a valuable tool to generate novel medicinal chemistry hypothesis. One can bias de novo generated molecules to a specific chemotype or a scaffold. Conversely, it also allows avoidance of particular chemical groups or substructures (like bromine or carboxyl group). Finally, one could use a substructure or pharmacophore similarity[42] reward to explore chemical space with finer granularity.

Table 1 shows a decrease in the proportion of the valid molecules after the optimization. We may explain this phenomenon by the weaknesses of predictive models P (See FIG. 1) and the integration of predictive and generative models into a single design system. We presume that the generative model G tends to find some local optima of the reward function that correspond to invalid molecules, but the predictive model P assigns high rewards to these molecules. This explanation is also supported by the results of structure bias optimization experiments, as we did not use any predictive models in these experiments and the decrease in the proportion of valid molecules was insignificant. We also noticed, that among all experiments with predictive models, those with Log P optimization showed the highest proportion of valid molecules and, at the same time, the predictive model for Log P estimation had the highest accuracy $R2=0.91$ (see Methods). It is probably harder for the RL system to exploit the high quality predictive model P and produce fictitious SMILES strings with predicted properties in the desired region.

TABLE 1

Comparison of statistics for optimized, untrained and training molecules datasets

| Property | | Valid molecules, % | Mean molar mass | Mean value of target property | Match with ZINC15 database[38], % | Match with ChEMBL database[43], % |
| --- | --- | --- | --- | --- | --- | --- |
| Melting temperature | untrained | 95 | 435.4 | 181.30 | 4.7 | 1.5 |
| | minimized | 31 | 279.6 | 137.17 | 4.6 | 1.6 |
| | maximized | 53 | 413.2 | 200.715 | 2.4 | 0.9 |
| pIC50 for jak2 kinase | untrained | 95 | 435.4 | 5.70 | 4.7 | 1.5 |
| | minimized | 60 | 481.8 | 4.89 | 2.5 | 1.0 |
| | maximized | 45 | 275.4 | 7.85 | 4.5 | 1.8 |
| log P | untrained | 95 | 435.4 | 3.63 | 4.7 | 1.5 |
| | optimized | 70 | 369.7 | 2.58 | 5.8 | 1.8 |
| Number of benzene rings | untrained | 95 | 435.4 | 0.59 | 4.7 | 1.5 |
| | optimized | 83 | 496.0 | 2.41 | 5.5 | 1.6 |
| Number of substituents | untrained | 95 | 435.4 | 3.8 | 4.7 | 1.5 |
| | optimized | 80 | 471.7 | 7.93 | 3.1 | 0.7 |

Figure 12:
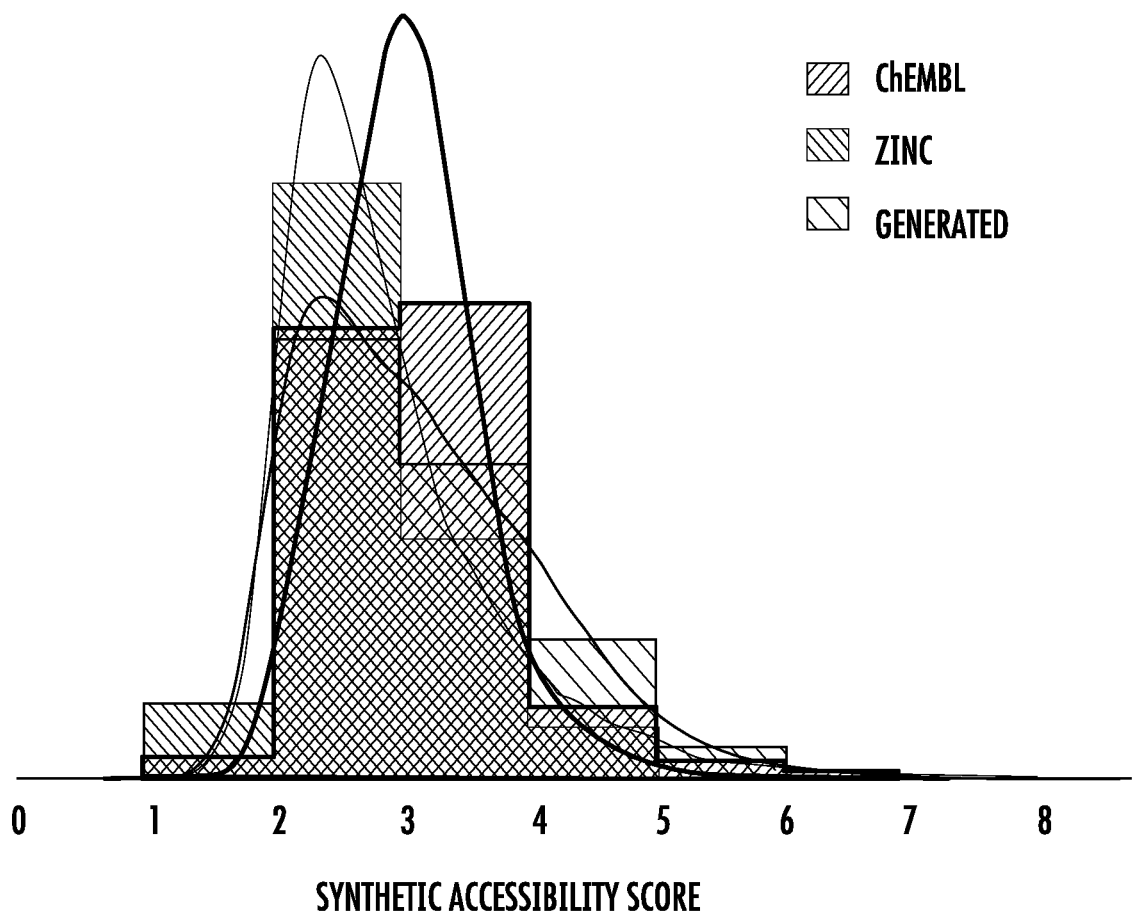
FIG. 12 illustrates distribution of a Synthetic Accessibility Score (SAS) for the full ChEMBL21 database, random subsample of 1M molecules from ZINC15 and generated dataset of molecules with generator model G.

In addition to passing the structure checker, an important requirement for de novo generated molecules is their synthetic feasibility. To this end, we employed the synthetic accessibility score (SAS) method (41), which relies on the knowledge extracted from known synthetic reactions and adds a penalty for high molecular complexity. For ease of interpretation, SAS is scaled to be between 1 and 10. Molecules with the high SAS value, typically above 6, are considered difficult to synthesize, whereas, molecules with the low SAS values are easily synthetically accessible. The distribution of SAS values calculated for 1M molecules generated is shown in FIG. 12. To illustrate the robustness of the de novo generated chemical library, we compared its SAS distribution with that of the SAS values both for the full ChEMBL library (~1.5M molecules) and for a 1M random sample of molecules in ZINC. Similar to typical commercial vendor libraries, the distribution of SAS for generated compounds is skewed towards more easily synthesizable molecules. Median SAS values were 2.9 for ChEMBL and 3.1 for both ZINC and ReLeaSE. Over 99.5% of de novo generated molecules had SAS values below 6. Therefore, despite their high novelty, a vast majority of the generated compounds can be considered as synthetically accessible.

Figure 13:
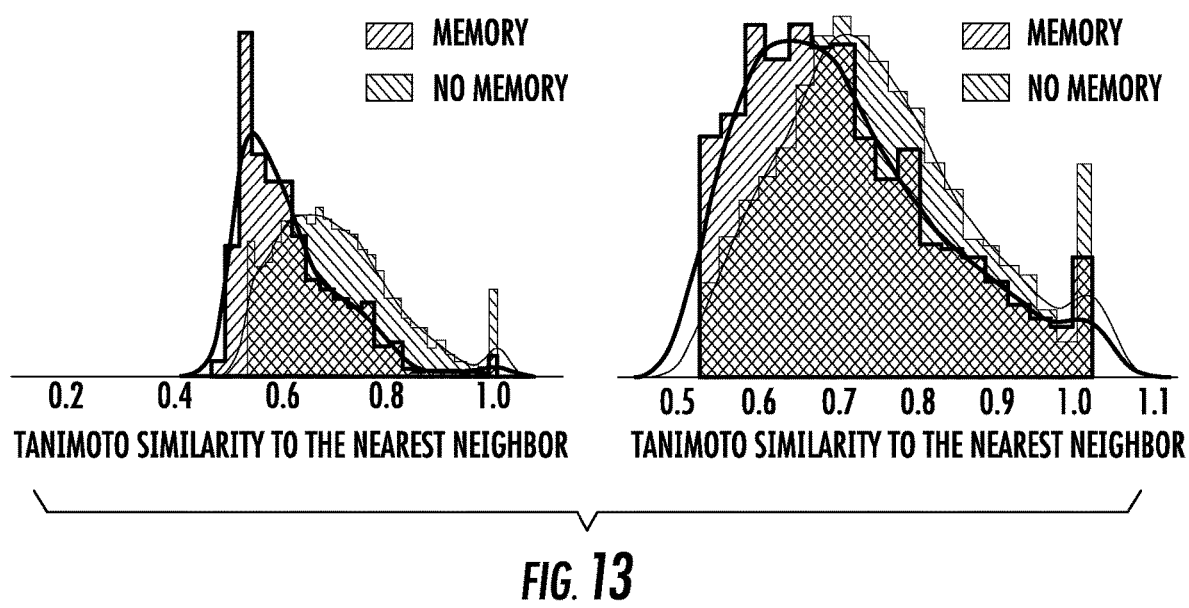
FIG. 13 illustrates performance of the generative model G, with and without stack-augmented memory. The left hand graph in FIG. 13 illustrates Internal diversity of generated libraries. The right hand graph in FIG. 13 illustrates similarity of the generated libraries to the training dataset from the ChEMBL database.

To assess the importance of using stack memory augmented network as described in the Methods, we compared several characteristics of chemical libraries generated by models developed either with or without stack memory. For this purpose, we trained another generative recurrent neural network with the same architecture but without using stack memory. Libraries were compared by the percentage of valid generated SMILES, internal diversity, and similarity of the generated molecules to those in the training dataset (ChEMBL). The model without stack memory showed that only 86% of molecules in the respective library were valid compared to 95% of valid molecules in the library generated with stack memory network. As expected (cf. the justification for using stack memory augmented network in Methods), in the former library, syntactic errors such as open brackets, unclosed cycles and incorrect bond types in SMILES strings were more frequent. Based on the analysis of respective sets of 10000 molecules generated by each method (See left hand graph in FIG. 13), the library obtained without stack memory showed a decrease of the internal diversity by 0.2 units of the Tanimoto coefficient and yet, a four-fold increase in the number of duplicates, from just about 1% to 5%. In addition, the right hand graph in FIG. 13 shows that the number of molecules similar to the training dataset (Ts>0.85) for library obtained without stack memory (28% of all molecules) is twice that obtained with stack memory (14%). These results clearly highlight the advantages of using a neural network with memory for generating the highest number of realistic and predominantly novel molecules, which is one of the chief objectives of de novo chemical design.

Model Analysis

Model interpretation is of utmost importance in any ML study. In this section, we demonstrate how the Stack-RNN learns and memorizes useful information from the SMILES string that it is currently processing. We manually analyzed neuron's gate activations of the neural network while it processes the input data.

Figure 6:
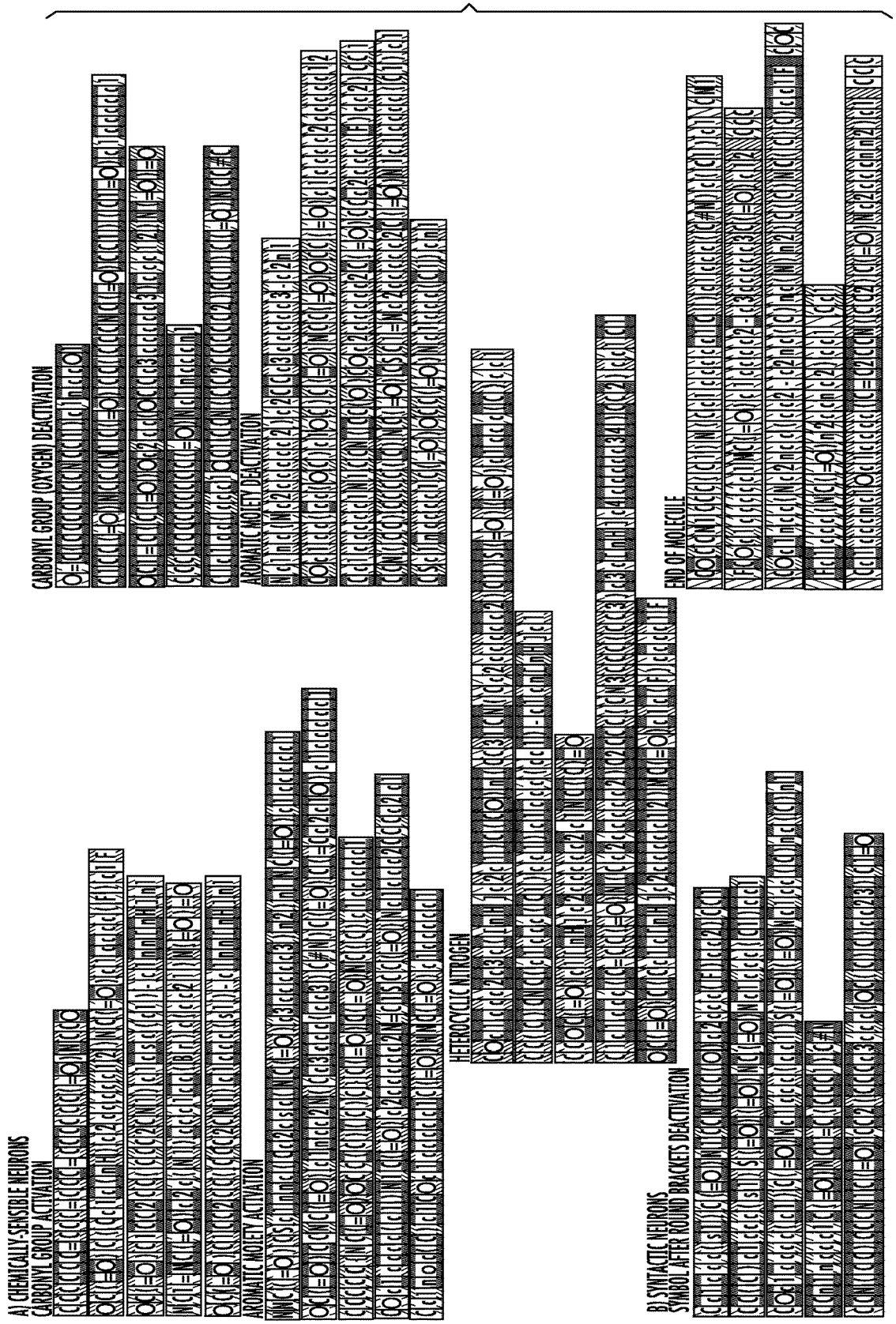
FIG. 6 illustrates example of Stack-RNN cells with interpretable gate activations.

FIG. 6 lists several examples of cells with interpretable gate activations. In FIG. 6, each line corresponds to activations of a specific neuron at different time steps of processing SMILES string. Each letter is colored according to the value of activation in a cool-warm color map from dark blue to dark red—from −1 to 1. We discovered that that our RNN has several interpretable cells, which can be divided into two groups—chemically sensible, that activates on specific chemical groups or moieties, and syntactic, that keep tracks on numbers, bracket opening and closure, or even keep track when the molecule ends. Unfortunately, a large portion of the cells do something that is not interpretable.

FIG. 6 illustrates examples of Stack-RNN cells with interpretable gate activations. The color-coding in FIG. 6 corresponds to GRU cells with a tan h activation function, where −1 is dark blue and 1 is red.

For instance, we see cells acting on presence of carbonyl group, aromatic groups or NH moiety in heterocycles. We also discovered that in two of these three examples there are counter-cells that deactivate in presence of the same chemical groups.

Figure 7A:
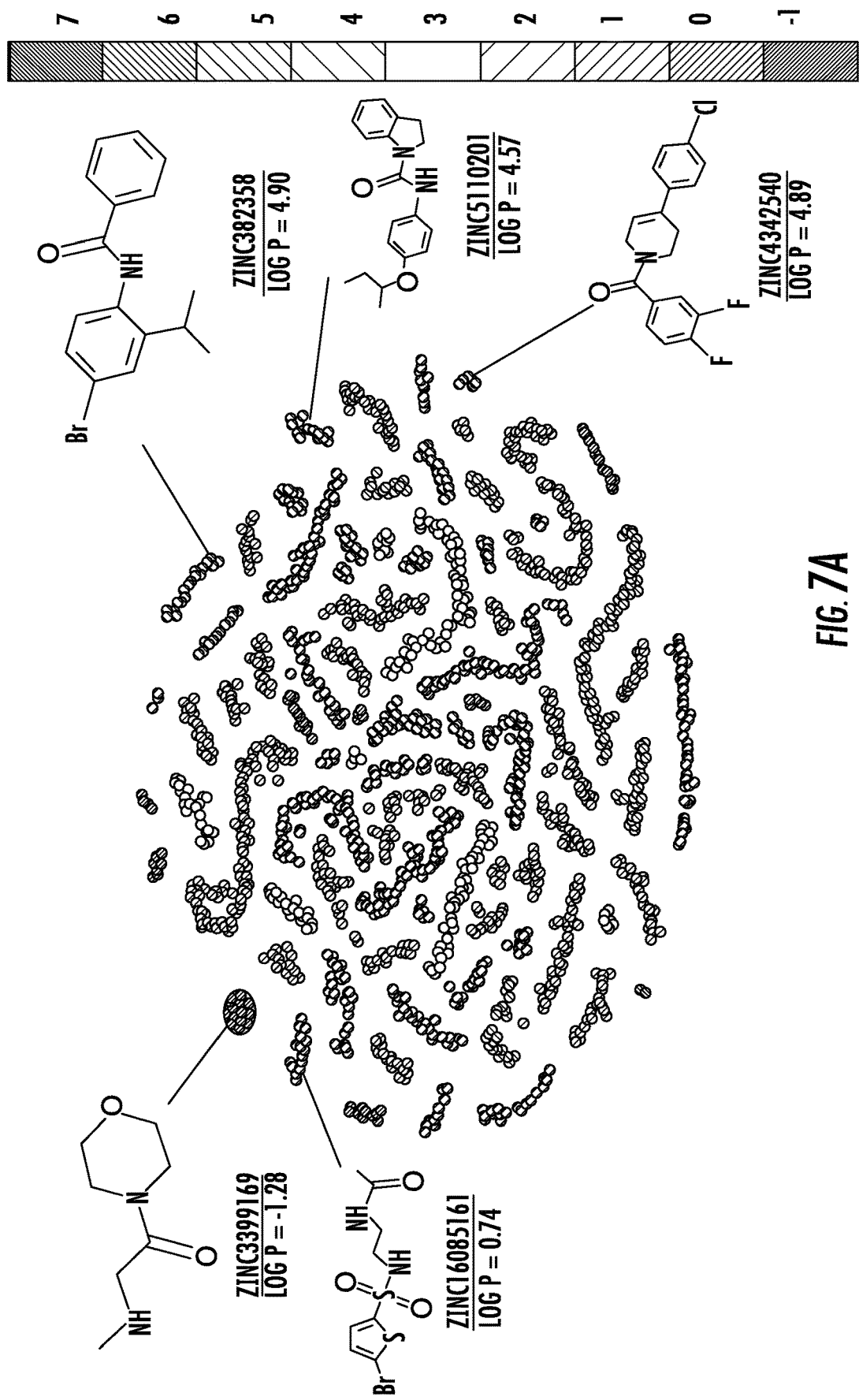
FIG. 7 illustrates clustering of generated molecules by T distributed stochastic neighbor embedding (T-SNE), where molecules are colored based on predicted properties by model P.
Figure 7B:
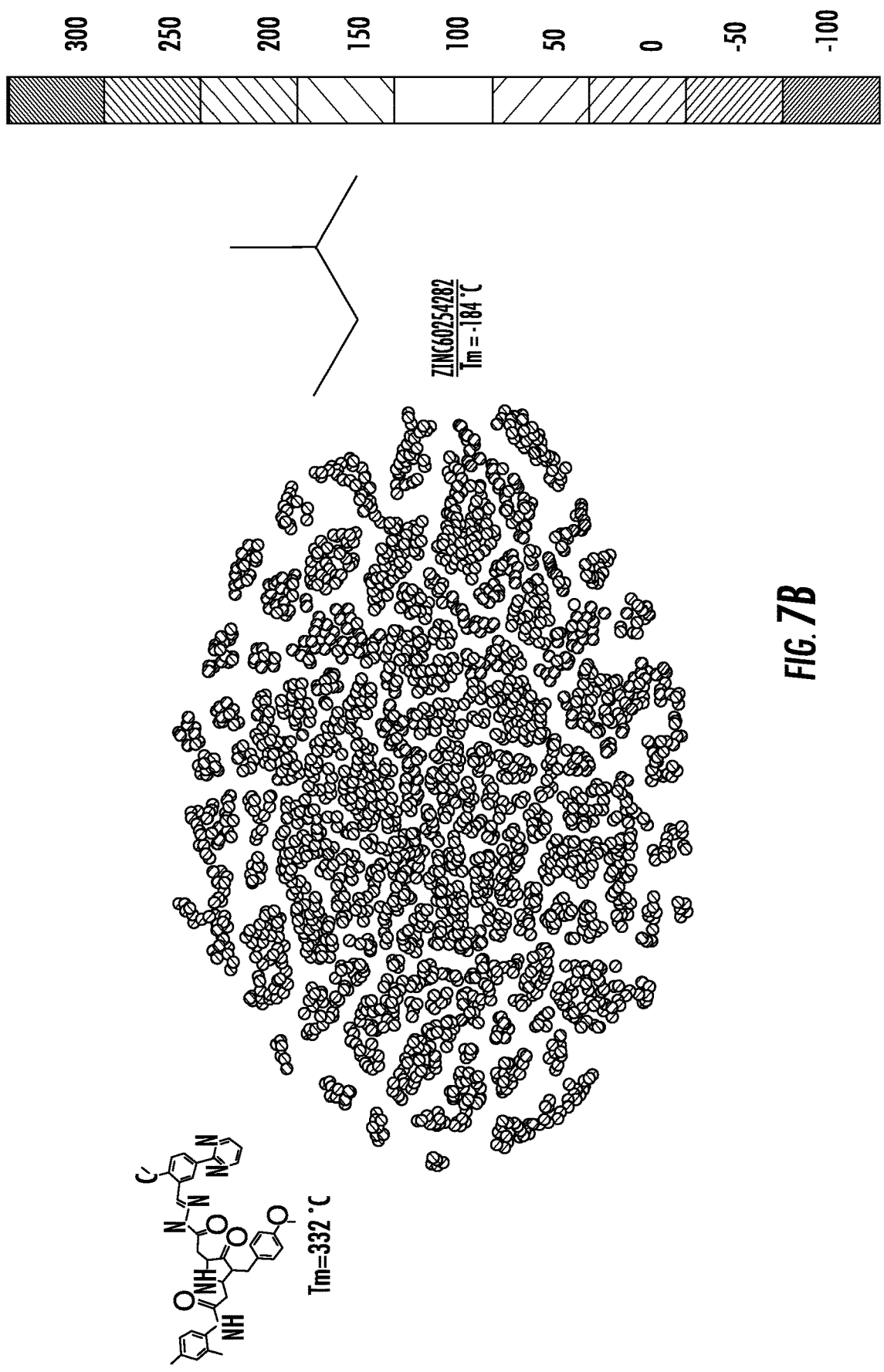
Figure 7C:
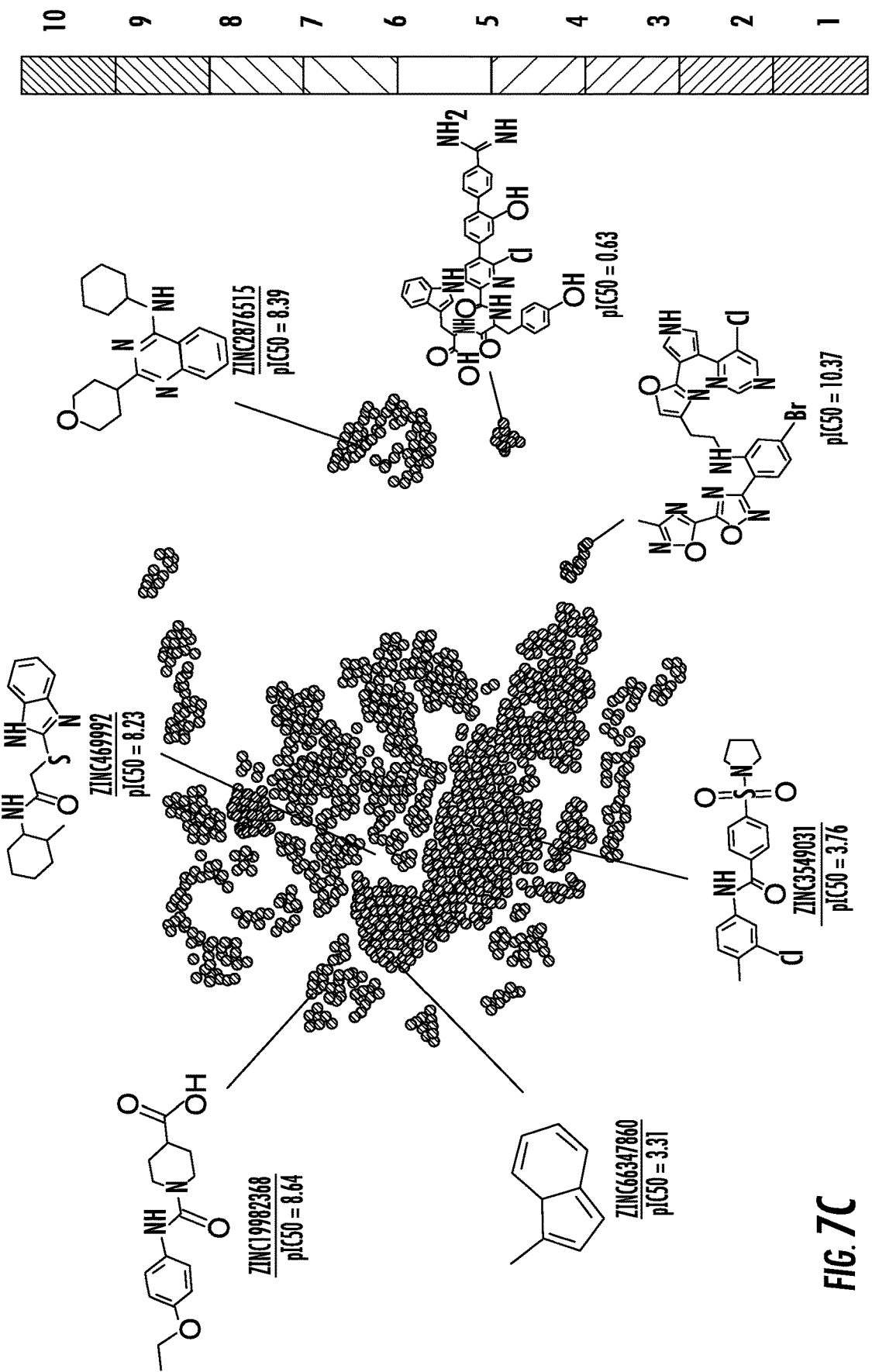

In order to understand the how the generative model populates chemical space, we used t-Distributed Stochastic Neighbor Embedding (t-SNE) for dimensionality reduction[44]. We selected datasets for three endpoints (melting temperature, JAK2 kinase and log P) produced with corresponding optimized generative models G. For every molecule, we calculated a latent vector of representation from the feed-forward layer with ReLU activation function in the predictive model P for the corresponding property and constructed a 2D projection using t-SNE. Obtained projections are illustrated in FIGS. 7A-7C. Every point corresponds to a molecule and is colored according to its property value.

The partition coefficient (FIG. 7A) is smoothly changing across the chemical space, and we can observe well defined clustering of molecules with similar log P. In contrast, for melting temperature (FIG. 7B) there are no such clusters. High and low $T_m$ molecules are intermixed together. This observation can be explained by the fact that melting temperature depends not only on a chemical structure of the molecule, but also on intermolecular forces between them and packing into the crystal lattice. Therefore, neural could not find optimal representation for this property. In the case of the JAK2 kinase model, we could observe two large non-overlapping areas roughly corresponding to inactive (pIC50<6) and active (pIC50>6) compounds.

Discussion

In this work, we propose a deep reinforcement learning approach for de novo molecular design. This strategy allows generating chemical compounds with desired properties. Two deep neural networks-generative and predictive, represent the general RL workflow. The process of training consists of two stages. During the first stage, both models are trained separately in a supervised learning fashion, and during the second stage, models are trained jointly with a reinforcement learning method. Both neural networks are end-to-end deep learning that do not rely on pre-defined chemical descriptors and can be trained directly from chemical structure as represented by SMILES strings.

This distinction makes our approach clearly differentiated from traditional QSAR methods. Therefore, it is very simple to set up and to use. This approach can be easily adapted to different chemical domains (industrial chemistry, polymers, etc.) or datasets (PubChem, in-house private data) with minimal modifications. It does not depend on domain knowledge or choice of a particular descriptor set.

As proof of principle, the model was tested on optimization of three diverse types of endpoints: physical properties, biological activity and chemical substructure bias. A flexible reward function could minimize, maximize or impose a desired range to a property of interest. We also released a dataset of over 1M of novel compounds that model "virtually synthesized".

In this study, we conducted computational experiments, which demonstrate the efficiency of proposed strategy in a single-task regime. I.e., each endpoint is optimized separately. However, typical drug discovery pipeline includes multi-objective optimization like potency, selectivity, solubility, ADMET properties, and so on. Our future work will be focused in this direction too. Nevertheless, the multiobjective optimization could be expressed as a combination between multiple tasks of three types we described.

Methods

Data. The melting point dataset was extracted from literature.[45] The PHYSPROP database[46] used to extract the octanol/water partition coefficient, log P for a diverse set of molecules. Experimental IC50 data tested against JAK2 kinase (CHEMBL ID 2971) was extracted from ChEMBL[43], PubChem[47] and in-house private databases. Compounds that had inconclusive IC50 values were considered unreliable and were not included in the modeling.

Data curation. Compiled datasets of compounds were carefully curated following the protocols proposed by Fourches et al.[48] Briefly, explicit hydrogens were added, whereas specific chemotypes, such as aromatic and nitro groups, were normalized using the ChemAxon Standardizer. Polymers, inorganic salts, organometallic compounds, mixtures, and duplicates were removed. The modeling-ready curated dataset contained 14, 176 compounds for log P, 15,549 compounds for JAK2 kinase and 47,425 for melting temperature.

Figure 8A:
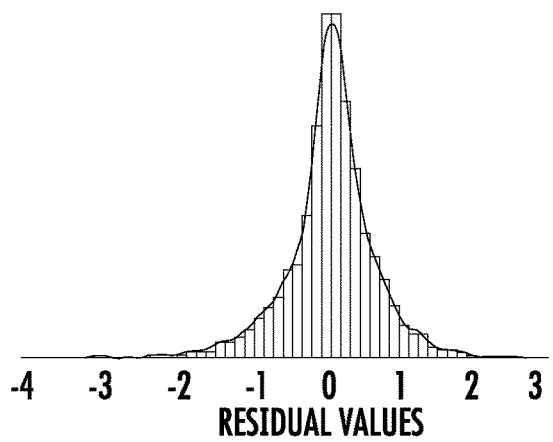
FIG. 8 illustrates distributions of residuals for predictive models.
Figure 8A:
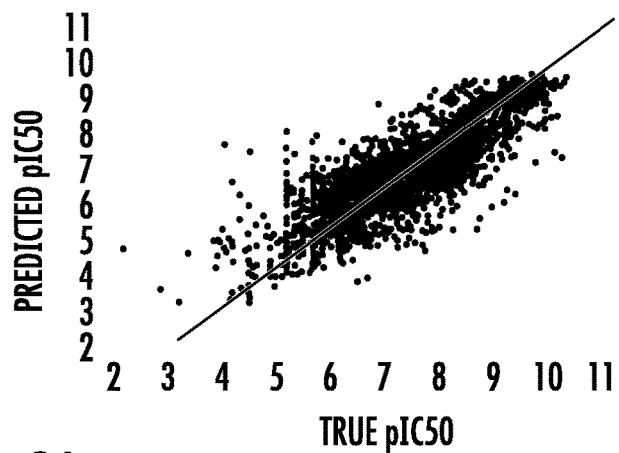
Figure 8B:
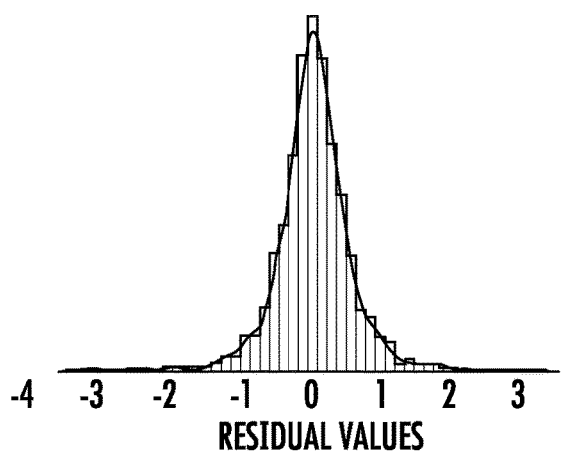
Figure 8B:
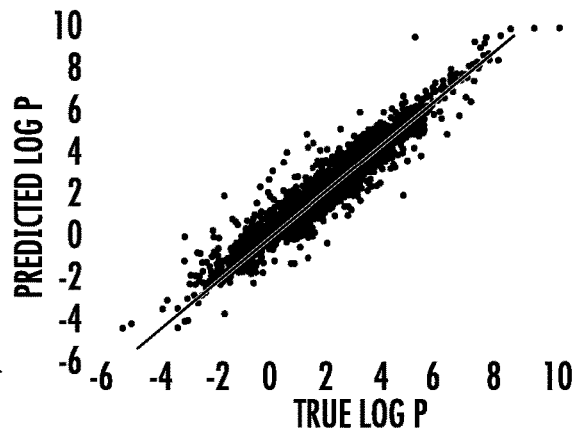
Figure 8C:
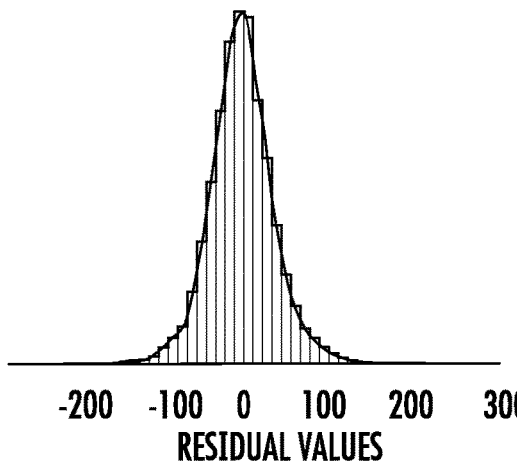
Figure 8C:
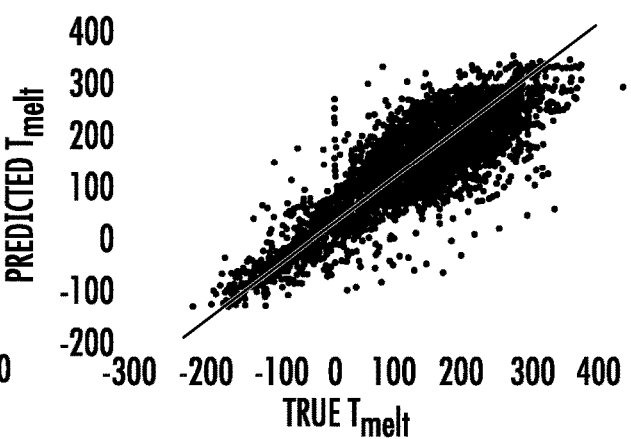

Predictive models. We trained predictive models for three different properties—melting temperature, log P and pIC50 for jak2 kinase. Each model consists of an embedding layer, which transforms sequence of discrete tokens into a vector of 100 continuous numbers, an LSTM layer with 100 units and tan h nonlinearity, one dense layer with 100 units and a rectify nonlinearity function and one dense layer with one unit and an identity activation function. All three models were trained with learning rate decay technique until convergence. Curated datasets were divided into training and validation sets in a ratio of 3:1. The results and accuracy of the model are shown in FIGS. 8A-8C.

Training

Figure 10:
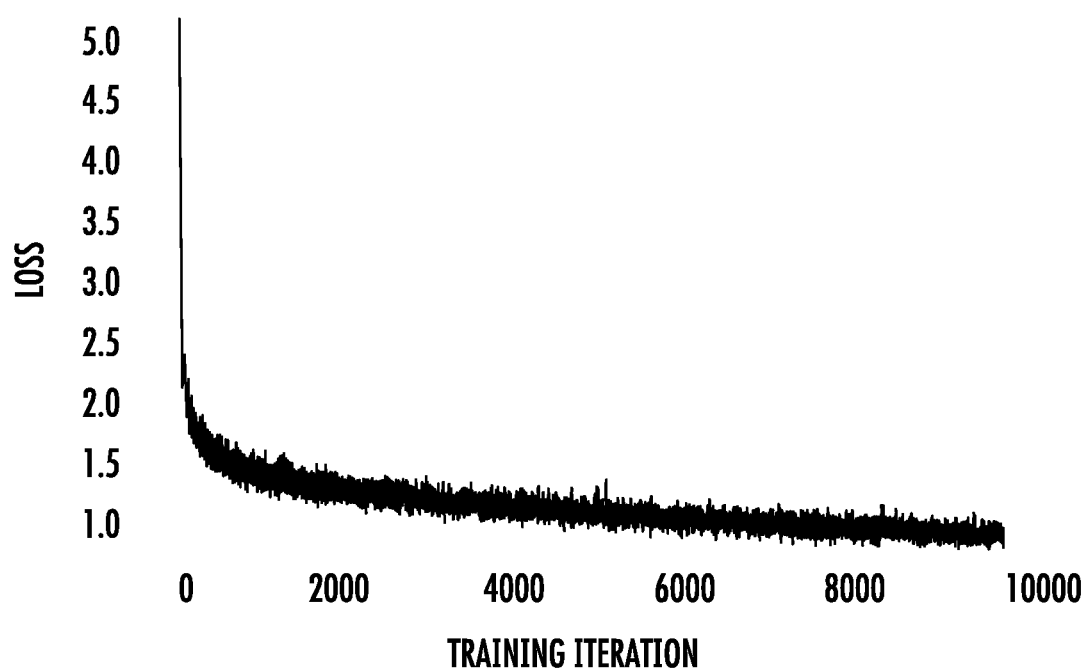
FIG. 10 illustrates a learning curve for the generative model.
Figure 11A:
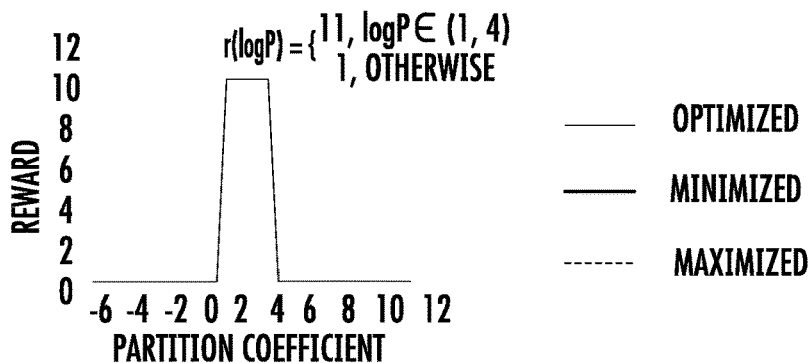
FIG. 11 illustrates graphs of reward functions.
Figure 11B:
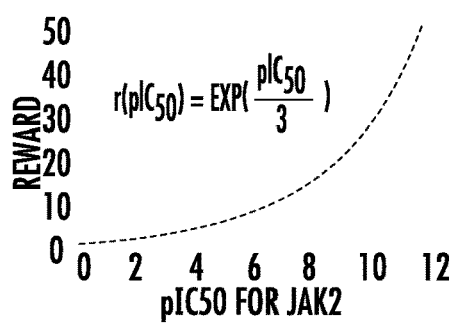
Figure 11E:
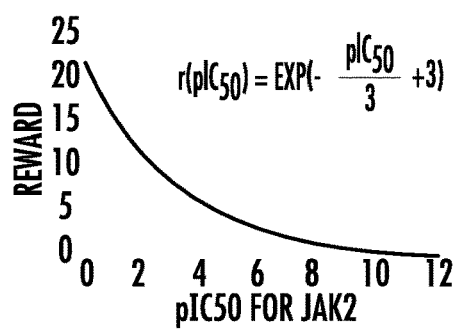
Figure 11C:
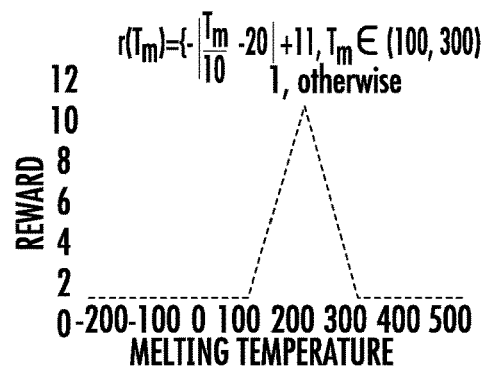
Figure 11F:
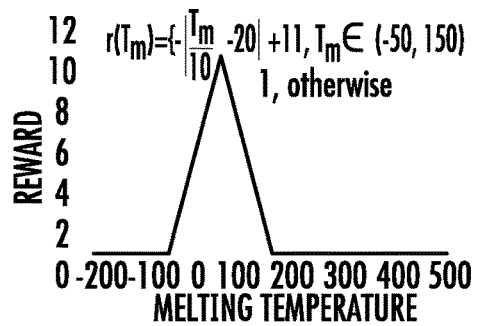
Figure 11D:
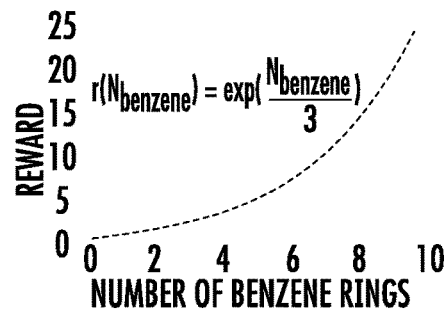
Figure 11G:
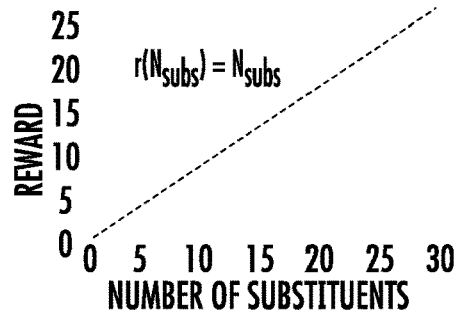

In the first stage, we pretrain a generative model on a ChEMBL21[43] dataset of approximately 1.5M drug-like compounds, so that the model is capable of producing chemically feasible molecules, but without property optimization. This network has 1500 units in recurrent GRU32 layer and 512 units in stack augmentation layer. The model was trained on GPU for 10000 epochs. The learning curve is illustrated in FIG. 10.

The generative model has two modes of processing sequences-training and generating. In training mode at each time step, the generative network takes a current prefix of the training object and predicts the probability distribution of next character. Then, the next character is sampled from this predicted probability distribution and is compared to the ground truth. Afterwards, based on this comparison, the cross-entropy loss function is calculated and parameters of the model are updated. In generating mode, at each time step, the generative network takes a prefix of the already generated sequence and then, similar to training mode, predicts probability distribution of next character and samples it from this predicted distribution. In generating model, we do not update model parameters.

In the second training stage, we combine both the generative and predictive models into one reinforcement learning system. In this system, the generative model plays the role of agent, whose action space is represented by the SMILES notation alphabet and state space is represented by all possible strings in this alphabet. The predictive model plays the role of critic, which estimates the agent's behavior by assigning a numerical reward to every generated molecule. The reward is a numerical function of a property predicted by predictive model. At this stage, the generative model is trained to maximize the expected reward. The whole pipeline is illustrated in FIG. 1.

Figure 9A:
FIG. 9 illustrates initial (left) and truncated (right) distributions of SMILES links.
Figure 9B:
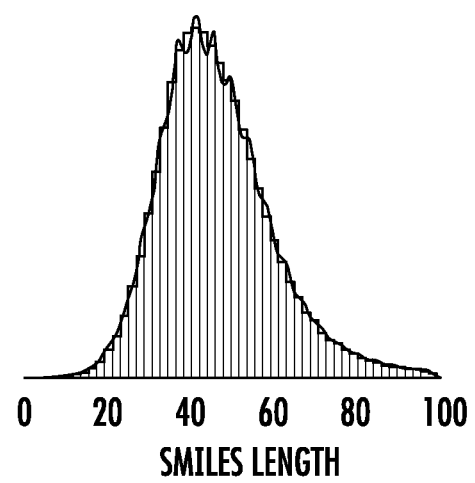

We trained a stack-augmented RNN as a generative model. As a training dataset, we took ChEMBL database of drug-like compounds, which includes approximately 1.5 million SMILES strings. For training, we selected from the initial training dataset only those molecules for which the SMILES notation length was less than 100 characters. The length of 100 was chosen because more than 97% of SMILES strings the training dataset were 100 characters or less (see FIG. 9).

Stack-augmented recurrent neural network. This section describes generative model G in more detail. We assume that the data is sequential, which means that it comes in the form of discrete tokens, for example, characters. The goal is to build a model, which is able to predict the next token taking all the previous ones. The regular recurrent neural network has an input layer and a hidden layer. At time step $t$, the neural network takes the embedding vector of token number $t$ from the sequence as an input and models the probability distribution of the next token given all previous tokens, so that the next token can be sampled from this distribution. Information of all previously observed tokens is aggregated in the hidden layer. This can be written as follows:

$$h_t = \sigma(W_i x_t + W_h h_{t-1}),$$

where $h_t$ is a vector of hidden states, $h_{t-1}$—vector of hidden states from the previous time step, $x_t$—input vector at time step t, $W_i$—parameters of the input layers, $W_h$—parameters of the hidden layer and σ—activation function.

The stack memory is used to keep the information and deliver it to the hidden layer at the next time step. A stack is a type of persistent memory which can be only accessed through its topmost element. There are three basic operations supported by the stack: a POP operation, which deletes an element from the top of the stack, a PUSH operation, which puts a new element to the top of our stack and also a NO—OP operation, which performs no action. The top element of the stack has value $s_t[0]$ and is stored at position 0:

$$s_t[0] = a_t[PUSH]\sigma(Dh_t) + a_t[POP]s_{t-1}[1] + a_t[NO-OP]$$
$$s_{t-1}[0].$$

where D is 1×m matrix and $a_t = [a_t[PUSH], a_t[POP], a_t[NO-OP]]$ is a vector of stack control variables, which define the next operation to be performed. If $a_t[POP]$ is equal to 1, then the value below is used to replace the top element of the stack. If $a_t[PUSH]$ is equal to 1, then a new value will be added to the top and all the rest of the values will be moved down. If $a_t[NO-OP]$ equals 1 then the stack keeps the same value on top.

A similar rule is applied to the elements of the stack at a depth i>0:

$$s_t[i] = a_t[PUSH]s_{t-1}[i-1] + a_t[POP]s_{t-1}[i+1] + a_t[NO-OP] s_{t-1}[i].$$

Now the hidden layer $h_t$ is updated as:

$$h_t = \sigma(U_{x_t} + Rh_{t-1} + Ps_{t-1}^k),$$

where P is a matrix of size m×k and $s_{t-1}^k$ are the first $k$ elements for the top of the stack at time step t−1.

The disclosure of each of the following references is incorporated herein by reference in its entirety.

REFERENCES (1) Scannell, J. W.; Blanckley, A.; Boldon, H.; Warrington, B. Diagnosing the Decline in Pharmaceutical R&D Efficiency. *Nat. Rev. Drug Discov.* 2012, 11, 191-200.
(2) Artificial intelligence: The return of the machinery question http://www.economist.com/news/special-report/21700761-after-many-false-starts-artificial-intelligence-has-taken-will-it-cause-mass (accessed Feb. 23, 2017).
(3) Jha, S.; Topol, E. J. Adapting to Artificial Intelligence. *JAMA* 2016, 316, 2353.
(4) Chockley, K.; Emanuel, E. The End of Radiology? Three Threats to the Future Practice of Radiology. *J. Am. Coll. Radiol.* 2016, 13, 1415-1420.
(5) Ragoza, M.; Hochuli, J.; Idrobo, E.; Sunseri, J.; Koes, D. R. Protein-Ligand Scoring with Convolutional Neural Networks. *J. Chem. Inf. Model.* 2017, 57, 942-957.
(6) Altae-Tran, H.; Ramsundar, B.; Pappu, A. S.; Pande, V. Low Data Drug Discovery with One-Shot Learning. *ACS Cent. Sci.* 2017, 3, 283-293.
(7) Segler, M. H. S.; Waller, M. P. Modelling Chemical Reasoning to Predict and Invent Reactions. *Chem.—A Eur. J.* 2017, 23, 6118-6128.
(8) Smith, J. S.; Isayev, O.; Roitberg, A. E. ANI-1: An Extensible Neural Network Potential with DFT Accuracy at Force Field Computational Cost. *Chem. Sci.* 2017, 8, 3192-3203.
(9) Schnecke, V.; Boström, J. Computational Chemistry-Driven Decision Making in Lead Generation. *Drug Discovery Today,* 2006, 11, 43-50.
(10) Macarron, R. Critical Review of the Role of HTS in Drug Discovery. *Drug Discovery Today.* 2006, pp. 277-279.
(11) Schneider, G.; Fechner, U. Computer-Based de Novo Design of Drug-like Molecules. *Nat. Rev. Drug Discov.* 2005, 4, 649-663.
(12) Mauser, H.; Guba, W. Recent Developments in de Novo Design and Scaffold Hopping. *Curr. Opin. Drug Discov. Devel.* 2008, 11, 365-374.
(13) Ruddigkeit, L.; van Deursen, R.; Blum, L. C.; Reymond, J.-L. Enumeration of 166 Billion Organic Small Molecules in the Chemical Universe Database GDB-17. *J. Chem. Inf. Model.* 2012, 52, 2864-2875.
(14) Polishchuk, P. G.; Madzhidov, T. I.; Varnek, A. Estimation of the Size of Drug-like Chemical Space Based on GDB-17 Data. *J. Comput. Aided. Mol. Des.* 2013, 27, 675-679.
(15) Lipinski, C.; Hopkins, A. Navigating Chemical Space for Biology and Medicine. *Nature* 2004, 432, 855-861.
(16) Reker, D.; Schneider, G. Active-Learning Strategies in Computer-Assisted Drug Discovery. *Drug Discov. Today* 2015, 20, 458-465.
(17) Schneider, P.; Schneider, G. De Novo Design at the Edge of Chaos. *J. Med. Chem.* 2016, 59, 4077-4086.
(18) Brown, N.; Mckay, B.; Gilardoni, F.; Gasteiger, J. A Graph-Based Genetic Algorithm and Its Application to the Multiobjective Evolution of Median Molecules. *J. Chem. Inf. Comput. Sci.* 2004, 44, 1079-1087.
(19) Gómez-Bombarelli, R.; Duvenaud, D.; Hernández-Lobato, J. M.; Aguilera-Iparraguirre, J.; Hirzel, T. D.; Adams, R. P.; Aspuru-Guzik, A. Automatic Chemical Design Using a Data-Driven Continuous Representation of Molecules. arXiv ID 1610.02415 2016, 1-23.
(20) Segler, M. H. S.; Kogej, T.; Tyrchan, C.; Waller, M. P. Generating Focussed Molecule Libraries for Drug Discovery with Recurrent Neural Networks. 2017.
(21) De Asis, K.; Hernandez-Garcia, J. F.; Holland, G. Z.; Sutton, R. S. Multi-Step Reinforcement Learning: A Unifying Algorithm. 2017.
(22) Krakovsky, M. Reinforcement Renaissance. *Commun. ACM* 2016, 59, 12-14.
(23) Silver, D.; Huang, A.; Maddison, C. J.; Guez, A.; Sifre, L.; van den Driessche, G.; Schrittwieser, J.; Antonoglou, I.; Panneershelvam, V.; Lanctot, M.; et al. Mastering the Game of Go with Deep Neural Networks and Tree Search. *Nature* 2016, 529, 484-489.
(24) van den Herik, H. J.; Uiterwijk, J. W. H. M.; van Rijswijck, J. Games Solved: Now and in the Future. *Artif. Intell.* 2002, 134, 277-311.
(25) Willia, R. J. Simple Statistical Gradient-Following Algorithms for Connectionist Reinforcement Learning. *Mach. Learn.* 1992, 8, 229-256.
(26) Goodfellow, I.; Pouget-Abadie, J.; Mirza, M.; Xu, B.; Warde-Farley, D.; Ozair, S.; Courville, A.; Bengio, Y. Generative Adversarial Nets. *Adv. Neural Inf. Process. Syst.* 27 2014, 2672-2680.
(27) Yu, L.; Zhang, W.; Wang, J.; Yu, Y. SeqGAN: Sequence Generative Adversarial Nets with Policy Gradient. arXiv 2016.
(28) Martens, J. Generating Text with Recurrent Neural Networks. *Neural Networks* 2011, 131, 1017-1024.
(29) Weininger, D. SMILES, a Chemical Language and Information System. 1. Introduction to Methodology and Encoding Rules. *J. Chem. Inf. Comput. Sci.* 1988, 28, 31-36.
(30) Joulin, A.; Mikolov, T. Inferring Algorithmic Patterns with Stack-Augmented Recurrent Nets. arXiv 2015, 1-10.
(31) Hochreiter, S.; Schmidhuber, J. J. Long Short-Term Memory. *Neural Comput.* 1997, 9, 1-32.
(32) Chung, J.; Gulcehre, C.; Cho, K.; Bengio, Y. Empirical Evaluation of Gated Recurrent Neural Networks on Sequence Modeling. arXiv 2014, 1-9.
(33) Deleu, T.; Dureau, J. Learning Operations on a Stack with Neural Turing Machines. arXiv 2016, 1-6.
(34) Berstel, J. Transductions and *Context-Free Languages*; Vieweg+Teubner Verlag: Wiesbaden, 1979.
(35) Grefenstette, E.; Hermann, K. M.; Suleyman, M.; Blunsom, P. Learning to Transduce with Unbounded Memory. arXiv 2015, 12.
(36) Mikolov, T.; Chen, K.; Corrado, G.; Dean, J. Distributed Representations of Words and Phrases and Their Compositionality. *Nips* 2013, 1-9.
(37) ChemAxon. Marvin Sketch.
(38) Irwin, J. J.; Shoichet, B. K. ZINC-A Free Database of Commercially Available Compounds for Virtual Screening. *J. Chem. Inf. Model.* 2005, 45, 177-182.
(39) Bemis, G. W.; Murcko, M. A. The Properties of Known Drugs. 1. Molecular Frameworks. *J. Med. Chem.* 1996, 39, 2887-2893.
(40) Sakatsume, M.; Igarashi, K.; Winestock, K. D.; Garotta, G.; Larner, A. C.; Finbloom, D. S. The Jak Kinases Differentially Associate with the Alpha and Beta (Accessory Factor) Chains of the Interferon Gamma Receptor to Form a Functional Receptor Unit Capable of Activating STAT Transcription Factors. *J. Biol. Chem.* 1995, 270, 17528-17534.
(41) Kralovics, R.; Passamonti, F.; Buser, A. S.; Teo, S.-S.; Tiedt, R.; Passweg, J. R.; Tichelli, A.; Cazzola, M.; Skoda, R. C. A Gain-of-Function Mutation of JAK2 in Myeloproliferative Disorders. *N. Engl. J. Med.* 2005, 352, 1779-1790.
(42) Stumpfe, D.; Bajorath, J. Similarity Searching. *Wiley Interdiscip. Rev. Comput. Mol. Sci.* 2011, 1, 260-282.

(43) Bento, A. P.; Gaulton, A.; Hersey, A.; *Bellis*, L. J.; Chambers, J.; Davies, M.; Krüger, F. A.; Light, Y.; Mak, L.; McGlinchey, S.; et al. The ChEMBL Bioactivity Database: An Update. *Nucleic Acids Res.* 2014, 42.

(44) Van Der Maaten, L. J. P.; Hinton, G. E. Visualizing High-Dimensional Data Using T-Sne. *J. Mach. Learn. Res.* 2008, 9, 2579-2605.

(45) Tetko, I. V; Sushko, Y.; Novotarskyi, S.; Patiny, L.; Kondratov, I.; Petrenko, A. E.; Charochkina, L.; Asiri, A. M. How Accurately Can We Predict the Melting Points of Drug-like Compounds? *J. Chem. Inf. Model.* 2014, 54, 3320-3329.

(46) Beauman, J. A.; Howard, P. H. Physprop Database. *Syracuse Res. Syracuse, NY, USA* 1995.

(47) Wang, Y.; Bryant, S. H.; Cheng, T.; Wang, J.; Gindulyte, A.; Shoemaker, B. A.; Thiessen, P. A.; He, S.; Zhang, J. PubChem BioAssay: 2017 Update. *Nucleic Acids Res.* 2017, 45, D955-D963.

(48) Fourches, D.; Muratov, E.; Tropsha, A. Trust, but Verify: On the Importance of Chemical Structure Curation in Cheminformatics and QSAR Modeling Research. *J Chem Inf Model* 2010, 50, 1189-1204.

It will be understood that various details of the subject matter described herein may be changed without departing from the scope of the subject matter described herein. Furthermore, the foregoing description is for the purpose of illustration only, and not for the purpose of limitation, as the subject matter described herein is defined by the claims as set forth hereinafter.

What is claimed is:

1. A system for automated design of molecules using artificial intelligence, the system comprising:
    a computing platform including at least one processor and a memory;
    a generative model implemented by the at least one processor for utilizing a first artificial neural network trained in a first training stage to generate representations of valid molecules in a predetermined notation, wherein the first artificial neural network comprises a stack-augmented recurrent neural network trained to model valences of atoms and sequence dependencies including ring openings, ring closures, and bracket sequences to generate the representations of the valid molecules;
    a predictive model implemented by the at least one processor and trained in the first training stage separately from the training of the generative model in the first training stage for predicting, from the representations of the valid molecules, numerical properties of the valid molecules; and
    a reward function implemented by the at least one processor for generating reward values for the valid molecules, where the reward values are functions of the predicted numerical properties generated by the trained predictive model and a user-specified property, wherein the generative model and the predictive model are trained jointly in a second training stage utilizing the reward values to teach the first artificial neural network to output representations of the valid molecules having the user-specified property,
    wherein, in the second training stage, the generative and predictive models are combined into a single reinforcement learning system in which the generative model operates as an agent whose action space is represented by a simplified molecular input line entry system (SMILES) notation alphabet and state space is represented by all possible strings in the SMILES notation alphabet and the predictive model operates as a critic which estimates behavior of the agent by assigning a reward value to each representation of one of the valid molecules generated by the generative model, and
    wherein the predictive model includes an embedding layer, a long short term memory layer, and two dense layers.

2. The system of claim 1 wherein the first artificial neural network utilizes a deep learning method.

3. The system of claim 1 wherein the predictive model utilizes a second neural network designed to predict the properties of the valid molecules from the representations of the valid molecules in the predetermined notation.

4. The system of claim 1 wherein at least some of the valid molecules whose representations are generated by the generative model are novel chemical entities.

5. The system of claim 1 wherein the representations of valid molecules generated by the generative model represent molecules that can be synthesized.

6. The system of claim 1 wherein the generative model is configured to generate libraries of the representations of the valid molecules with desired profiles of properties.

7. The system of claim 1 wherein the user-specified property comprises a chemical property, a physical property, or a biological property.

8. The system of claim 7 wherein the user-specified property comprises a biological activity.

9. A method for automated design of molecules using artificial intelligence, the method comprising:
    training, in a first training stage, a generative model comprising a first artificial neural network implemented by at least one processor to output representations of valid molecules in a predetermined notation, wherein the first artificial neural network comprises a stack-augmented recurrent neural network trained to model valences of atoms and sequence dependencies including ring openings, ring closures, and bracket sequences to generate the representations of the valid molecules;
    training, in the first training stage and separately from the training of the generative model in the first training stage, a predictive model comprising a second neural network to predict properties of the valid molecules in the predetermined notation;
    jointly training, in a second training stage, the generative model and the predictive model using reward values generated by a reward function which generates a reward value that is a function of a numerical property predicted by the trained predicted model to teach the first artificial neural network to output representations of the valid molecules having a user-specified property;
    utilizing the trained generative model including the first artificial neural network to generate representations of valid molecules in the predetermined notation; and
    utilizing the trained predictive model to predict properties of the valid molecules whose representations are output by the trained generative model,
    wherein, in the second training stage, the generative and predictive models are combined into a single reinforcement learning system in which the generative model operates as an agent whose action space is represented by a simplified molecular input line entry system (SMILES) notation alphabet and state space is represented by all possible strings in the SMILES notation alphabet and the predictive model operates as a critic which estimates behavior of the agent by assigning a reward value to each representation of one of the valid molecules generated by the generative model, and wherein the predictive model includes an embedding layer, a long short term memory layer, and two dense layers.

10. The method of claim 9 wherein the first artificial neural network utilizes a deep learning method.

11. The method of claim 9 wherein the predictive model utilizes a second neural network designed to predict the properties of the valid molecules from the representations of the valid molecules in the predetermined notation.

12. The method of claim 9 wherein at least some of the valid molecules whose representations are generated by the generative model are novel chemical entities.

13. The method of claim 9 wherein the user-specified property comprises a chemical property, a physical property, or a biological property.

14. The method of claim 13 wherein the user-specified property comprises a biological activity.

15. The method of claim 9 wherein the representations of the valid molecules generated by the generative model represent molecules that can be synthesized.

16. A non-transitory computer readable medium having stored thereon executable instructions that when executed by a processor of a computer control the computer to perform steps comprising:

training, in a first training stage, a generative model comprising a first artificial neural network to output valid molecules in a predetermined notation, wherein the first artificial neural network comprises a stack-augmented recurrent neural network trained to model valences of atoms and sequence dependencies including ring openings, ring closures, and bracket sequences to generate the representations of the valid molecules;

training, in the first training stage and separately from the training of the generative model in the first training stage, a predictive model comprising a second neural network to predict properties of molecules in the predetermined notation;

jointly training, in a second training stage, the generative model and the predictive model using reward values generated by a reward function which generates a reward value that is a function of a numerical property predicted by the trained predicted model to teach the first artificial neural network to output representations of the valid molecules having a user-specified property;

utilizing the trained generative model including the first artificial neural network to generate valid molecules in the predetermined notation; and utilizing the trained predictive model to predict properties of the molecules output by the trained generative model, wherein, in the second training stage, the generative and predictive models are combined into a single reinforcement learning system in which the generative model operates as an agent whose action space is represented by a simplified molecular input line entry system (SMILES) notation alphabet and state space is represented by all possible strings in the SMILES notation alphabet and the predictive model operates as a critic which estimates behavior of the agent by assigning a reward value to each representation of one of the valid molecules generated by the generative model, and wherein the predictive model includes an embedding layer, a long short term memory layer, and two dense layers.

* * * * *